(12) United States Patent
Kopin et al.

(10) Patent No.: US 6,376,198 B1
(45) Date of Patent: *Apr. 23, 2002

(54) ASSAY FOR NON-PEPTIDE AGONISTS TO PEPTIDE HORMONE RECEPTORS

(75) Inventors: Alan S. Kopin, Wellesley; Martin Beinborn, Brookline, both of MA (US)

(73) Assignee: New England Medical Center Hospitals, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/076,510

(22) Filed: May 12, 1998

(51) Int. Cl.$^7$ .................. G01N 33/53; C07K 14/705; C12N 15/62
(52) U.S. Cl. .............. 435/7.2; 435/69.7; 536/23.4
(58) Field of Search ............... 435/6.1, 7.1, 7.2, 435/69.7; 536/23.4

(56) References Cited

PUBLICATIONS

Tseng et al. Carboxyl–Terminal Domains Determine Internalization and Recycling Characteristics of Bombesin Receptor Chimeras. J Biol. Chem. 270(32):18858–18864, Aug. 1995.*

Jackson, Structure and Function of G Protein Coupled Receptors. Pharmacology and Therapeutics. 50:425–442, 1991.

Takaga et al. Structural Basis of G Protein Specificity of Human Endothelin Receptors. J. Biol. Chem. 270 (17):10072–10078, Apr. 1995.

Yokota et al. Delineation of Structural Domains Involved in the Subtype Specificity of Techykinin Receptors Through Chimeric Formation of Substance P/Substance K Receptors. Embo J. 11(10):3585–3591, Oct. 1992.

Sakamoto et al. Distinct Subdomains of Human Endothelin Receptors Determine Their Selectivity to Endothelin A–Selective Agonist and Endothelin B–Selective Agonists. J. Biol. Chem. 268(12):8547–8553, Apr. 1993.

* cited by examiner

*Primary Examiner*—John Ulm
(74) *Attorney, Agent, or Firm*—Clark & Elbing LLP

(57) ABSTRACT

The invention features a method for determining whether a candidate compound is a non-peptide agonist of a peptide hormone receptor. In this method, a candidate compound is exposed to a form of the peptide hormone receptor which has an enhanced ability to amplify the intrinsic activity of a non-peptide agonist. The second messenger signaling activity of the enhanced receptor is measured in the presence of the candidate compound, and compared to the second messenger signaling activity of the enhanced receptor measured in the absence of the candidate compound. A change in second messenger signaling activity indicates that the candidate compound is an agonist. An increase in second messenger signaling activity indicates that the compound is either a full or partial positive agonist; a decrease in second messenger signaling activity indicates that the compound is an inverse (also termed a 'negative') agonist.

8 Claims, 12 Drawing Sheets

FIG. 1

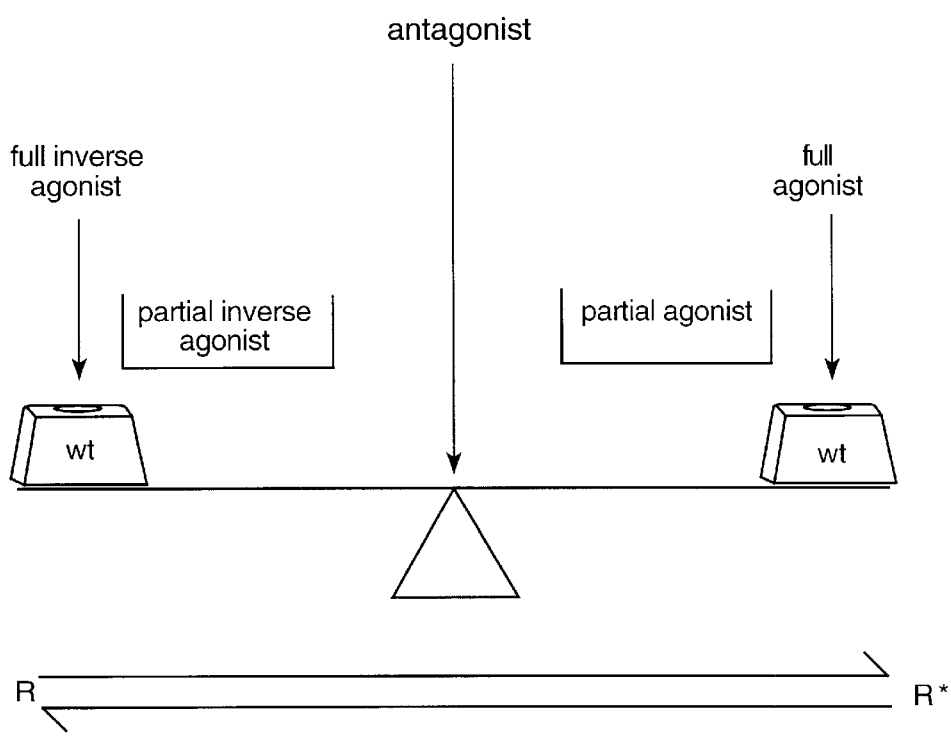

The position of the equilibrium between an inactive state R and an active state R* varies with individual receptors and is altered by the presence of receptor ligands. Agonists function by stabilizing R* while inverse agonists preferencially stabilize R. A continuum of ligands between full agonists (at the extreme right-hand side of the see-saw as these move the equilibrium furthest to the right) and full inverse agonists (at the extreme left-hand side of the see-saw) is expected to exist, with antagonists (which do not alter the position of the equilibrium at all) defining the position of the fulcrum.

FIG. 2A

MULTIPLE ALIGNMENT OF CLONED CCK RECEPTOR
DEDUCED AMINO ACID SEQUENCES

```
                      1                                                              50
Mastomys CCK-B        ........... ........ME LLKLNSSVQG PGPGSGSSLC RPGVSLLNSS
Rat CCK-B             ........... ........ME LLKLNRSVQG PGPGSGSSLC RPGVSLLNSS
Human CCK-B           ........... ........ME LLKLNRSVQG TGPGPGASLC RPGAPLLNSS
Canine CCK-B          ........... ........ME LLKLNRSAQG SGAGPGASLC RAGGALLNSS
Human CCK-A           ........... .....MDVVD SLLVNGSNIT PPCELGLEN. ..........
Rat CCK-A             MSHSPARQHL VESSRMDVVD SLLMNGSNIT PPCELGLEN. ..........
Xenopus CCK-XL        ......MESL RSLSNISALH ELLCRYSNLS GTLTWNLSST NGTHNLTTAN 51                                                             100
Mastomys CCK-B        SAGNLSCEPP RI..RGTGTR ELELAIRITL YAVIFLMSIG GNMLIIVVLG
Rat CCK-B             SAGNLSCDPP RI..RGTGTR ELEMAIRITL YAVIFLMSVG GNVLIIVVLG
Human CCK-B           SVGNLSCEPP RI..RGAGTR ELELAIRITL YAVIFLMSVG GNMLIIVVLG
Canine CCK-B          GAGNLSCEPP RL..RGAGTR ELELAIRVTL YAVIFLMSVG GNVLIIVVLG
Human CCK-A           ......ETLF CLDQPRPS.K EWQPAVQILL YSLIFLLSVL GNTLVITVLI
Rat CCK-A             ......ETLF CLDQPQPS.K EWQSALQILL YSIIFLLSVL GNTLVITVLI
Xenopus CCK-XL        WPPWNLNCTP ILDRKKPSPS DLNLWVRIVM YSVIFLLSVF GNTLIIIVLV 101                                                            150
Mastomys CCK-B        LSRRLRTVTN AFLLSLAVSD LLLAVACMPF TLLPNLMGTF IFGTVICKAV
Rat CCK-B             LSRRLRTVTN AFLLSLAVSD LLLAVACMPF TLLPNLMGTF IFGTVICKAI
Human CCK-B           LSRRLRTVTN AFLLSLAVSD LLLAVACMPF TLLPNLMGTF IFGTVICKAV
Canine CCK-B          LSRRLRTVTN AFLLSLAVSD LLLAVACMPF TLLPNLMGTF IFGTVVCKAV
Human CCK-A           RNKRMRTVTN IFLLSLAVSD LMLCLFCMPF NLIPNLLKDF IFGSAVCKTT
Rat CCK-A             RNKRMRTVTN IFLLSLAVSD LMLCLFCMPF NLIPNLLKDF IFGSAVCKTT
Xenopus CCK-XL        MNKRLRTITN SFLLSLALSD LMVAVLCMPF TLIPNLMENF IFGEVICRAA 151                    Ⓐ                                       200
Mastomys CCK-B        SYLMGVSVSV STLNLVAIAL ERYSAICRPL QARVWQTRSH AARVILATWL
Rat CCK-B             SYLMGVSVSV STLNLVAIAL ERYSAICRPL QARVWQTRSH AARVILATWL
Human CCK-B           SYLMGVSVSV STLSLVAIAL ERYSAICRPL QARVWQTRSH AARVIVATWL
Canine CCK-B          SYLMGVSVSV STLSLVAIAL ERYSAICRPL QARVWQTRSH AARVIIATWM
Human CCK-A           TYFMGTSVSV STFNLVAISL ERYGAICRPL QSRVWQTKSH ALKVIAATWC
Rat CCK-A             TYFMGTSVSV STFNLVAISL ERYGAICRPL QSRVWQTKSH ALKVIAATWC
Xenopus CCK-XL        AYFMGLSVSV STFNLVAISI ERYSAICNPL KSRVWQTRSH AYRVIAATWV 201                                                            250
Mastomys CCK-B        LSGLLMVPYP VYTVVQP.V. ..GPRVLQCM HRWPSARVRQ TWSVLLIMLL
Rat CCK-B             LSGLLMVPYP VYTMVQP.V. ..GPRVLQCM HRWPSARVQQ TWSVLLLLLL
Human CCK-B           LSGLLMVPYP VYTVVQP.V. ..GPRVLQCV HRWPSARVRQ TWSVLLLLLL
Canine CCK-B          LSGLLMVPYP VYTAVQPAG. ..GARALQCV HRWPSARVRQ TWSVLLLLLL
Human CCK-A           LSFTIMTPYP IYSNLVPFTK NNNQTANMCR FLLPNDVMQQ SWHTFLLLIL
Rat CCK-A             LSFTIMTPYP IYSNLVPFTK NNNQTANMCR FLLPSDAMQQ SWQTFLLLIL
Xenopus CCK-XL        LSSIIMIPYL VYNKTVTFPM KDRRVGHQCR LVWPSKQVQQ AWYVLLLTIL 251                                                            300
Mastomys CCK-B        FFIPGVVMAV AYGLISRELY LGLRFDGDND SDTQSRVRNQ GGLPGG..TA
Rat CCK-B             FFIPGVVIAV AYGLISRELY LGLHFDGEND SETQSRARNQ GGLPGG..AA
Human CCK-B           FFIPGVVMAV AYGLISRELY LGLRFDGDSD SDSQSRVRNQ GGL.......
Canine CCK-B          FFVPGVVMAV AYGLISRELY LGLRFDEDSD SE..SRVRSQ GGLRGG..AG
Human CCK-A           FLIPGIVMMV AYGLISLELY QGIKFEASQK KSAKER.... ..........
Rat CCK-A             FLLPGIVMVV AYGLISLELY QGIKFDASQK KSAKEK.... ..........
Xenopus CCK-XL        FFIPGVVMIV AYGLISRELY RGIQFEMDLN KEAKAH.... ..........
```

FIG. 2B

```
              301                                                          350
Mastomys CCK-B   PGPVHQNGGC RHVT.VAGED NDGCYVQLPR SR..LEMTTL TTPTPGPGLA
Rat CCK-B        PGPVHQNGGC RPVTSVAGED SDGCCVQLPR SR..LEMTTL TTPTPGPVPG
Human CCK-B      PGAVHQNGRC RPETGAVGED SDGCYVQLPR SRPALELTAL TA..PGPGSG
Canine CCK-B     PGPAPPNGSC RPEGGLAGED GDGCYVQLPR SRQTLELSAL TAPTPGPGGG
Human CCK-A      .....KPSTT SSGKY...ED SDGCYLQKTR PPRKLELRQL STGS.SSRAN
Rat CCK-A        .....KPSTG SSTRY...ED SDGCYLQKSR PPRKLELQQL SSGSGGSRLN
Xenopus CCK-XL   .....KNGVS TPTTIPSGDE GDGCYIQVTR RRNTMEMSTL .TPSVCTKMD 351       Ⓑ       Ⓒ                                         400
Mastomys CCK-B   ...S.ANQAK LLAKKRVVRM LLVIVLLFFL CWLPIYSANT WCAFDGPGAH
Rat CCK-B        ...PRPNQAK LLAKKRVVRM LLVIVLLFFL CWLPVYSVNT WRAFDGPGAQ
Human CCK-B      ...SRPTQAK LLAKKRVVRM LLVIVVLFFL CWLPVYSANT WRAFDGPGAH
Canine CCK-B     ...PRPYQAK LLAKKRVVRM LLVIVVLFFL CWLPLYSANT WRAFDSSGAH
Human CCK-A      RIRSNSSAAN LMAKKRVIRM LIVIVVLFFL CWMPIFSANA WRAYDTASAE
Rat CCK-A        RIRSSSSAAN LIAKKRVIRM LIVIVVLFFL CWMPIFSANA WRAYDTVSAE
Xenopus CCK-XL   RARINNSEAK LMAKKRVIRM LIVIVAMFFI CWMPIFVANT WKAFDELSAF 401                                                          450
Mastomys CCK-B   RALSGAPISF IHLLSYASAC VNPLVYCFMH RRFRQACLDT CARCCPRPPR
Rat CCK-B        RALSGAPISF IHLLSYVSAC VNPLVYCFMH RRFRQACLDT CARCCPRPPR
Human CCK-B      RALSGAPISF IHLLSYASAC VNPLVYCFMH RRFRQACLET CARCCPRPPR
Canine CCK-B     RALSGAPISF IHLLSYASAC VNPLVYCFMH RRFRQACLET CARCCPRPPR
Human CCK-A      RRLSGTPISF ILLLSYTSSC VNPIIYCFMN KRFRLGFMAT FPCCPNPGPP
Rat CCK-A        KHLSGTPISF ILLLSYTSSC VNPIIYCFMN KRFRLGFMAT FPCCPNPGPP
Xenopus CCK-XL   NTLTGAPISF IHLLSYTSAC VNPLIYCFMN KRFRKAFLGT FSSCIKP...

451                               485
Mastomys CCK-B   ARPRPLPDED PPTPSIASLS RLSYTTISTL GPG..
Rat CCK-B        ARPQPLPDED PPTPSIASLS RLSYTTISTL GPG*.
Human CCK-B      ARPRALPDED PPTPSIASLS RLSYTTISTL GPG*.
Canine CCK-B     ARPRPLPDED PPTPSIASLS RLSYTTISTL GPG*.
Human CCK-A      GARGEVGEEE EGGTTGASLS RFSYSHMSAS VPPQ*
Rat CCK-A        GVRGEVGEEE DGRTIRALLS RYSYSHMSTS APPP*
Xenopus CCK-XL   .CRNFRDTDE DIAATGASLS KFSYTTVSSL GPA*.
```

FIG. 4
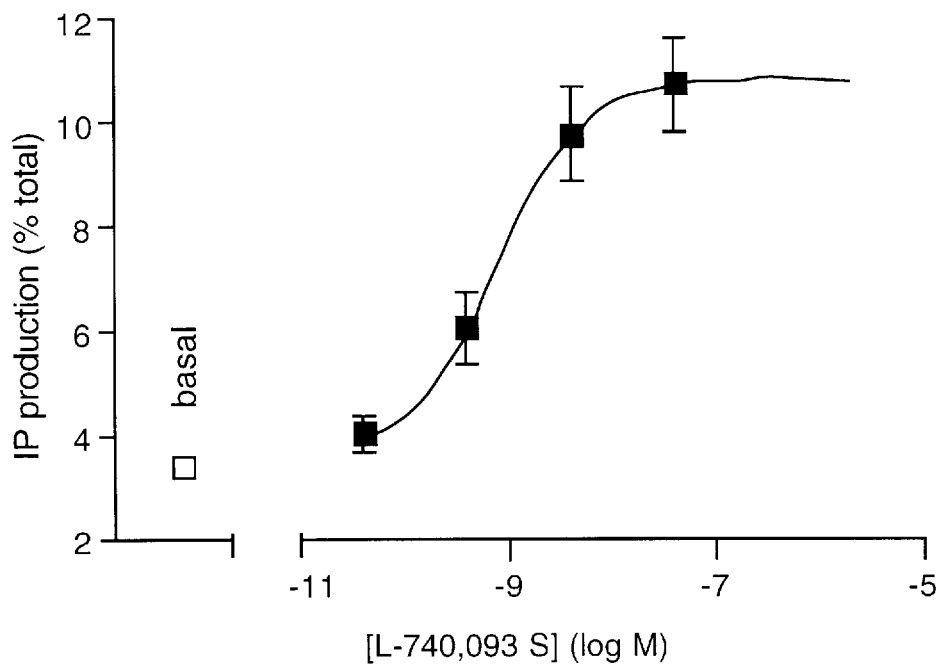
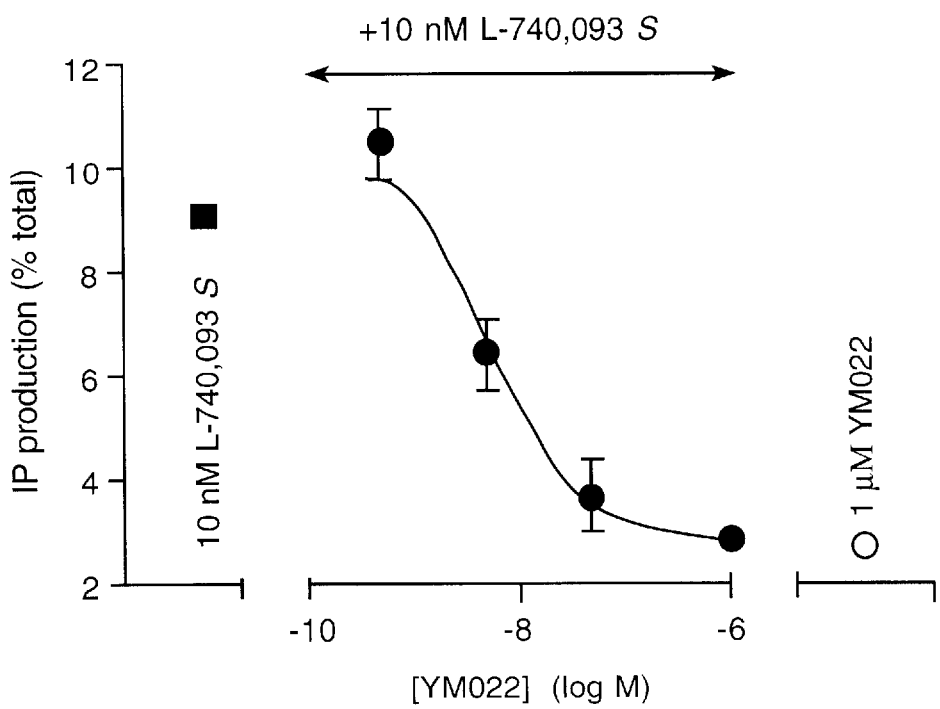

FIG. 5
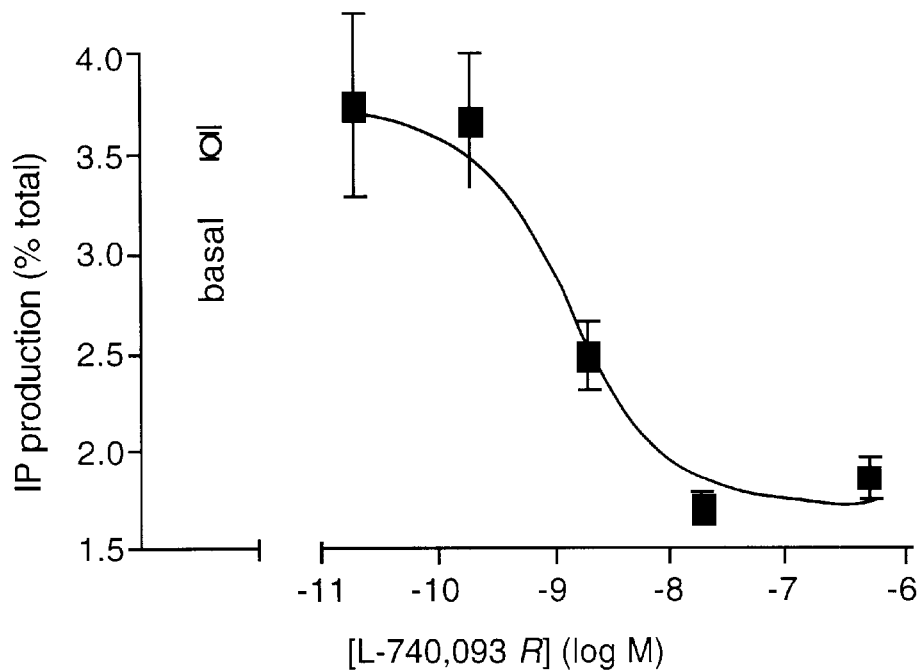
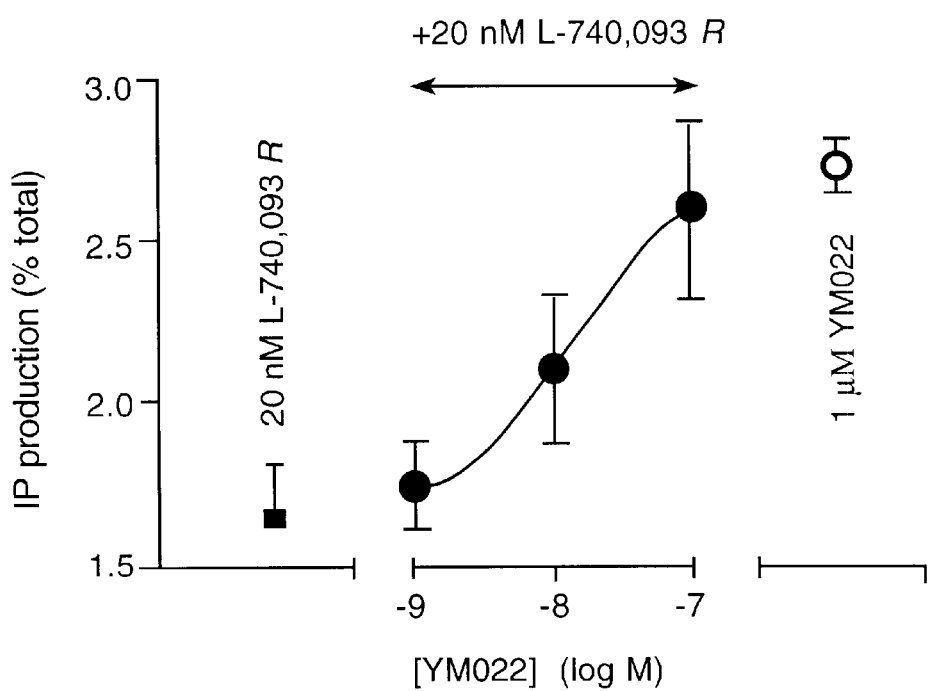

ASSAY FOR NON-PEPTIDE AGONISTS TO PEPTIDE HORMONE RECEPTORS

CROSS REFERENCE TO RELATED APPLICATIONS

The present application claims benefit of the filing date of U.S. Ser. No. 08/570,157, filed Dec. 11, 1995, now U.S. Pat. No. 5,750,353.

This invention was made in part with Government funding under National Institute of Health grant #DK46767, and the Government therefore has certain rights in the invention.

BACKGROUND OF THE INVENTION

This invention relates to peptide hormone receptors.

Peptide hormone receptors are important targets for drug research because a considerable number of diseases and other adverse effects result from abnormal receptor activity. High affinity, high specificity, non-peptide antagonists for peptide hormone receptors have been developed. These antagonists are therapeutically useful for decreasing receptor activation by endogenous hormones. Developing non-peptide agonists proved to be far more difficult.

One peptide hormone of interest, cholecystokinin (CCK), is a neuropeptide with two distinct receptors: CCK-A and CCK-B/gastrin (Vanderhaeghen et al., Nature, 257:604–605, 1975; Dockray, Nature, 264:568–570, 1976; Rehfeld, J. Biol. Chem., 253:4022–4030, 1978; Hill et al., Brain Res., 526:276–283, 1990; Hill et al., J. Neurosci., 10:1070–1081, 1990; Woodruff et al., Neuropeptides, (Suppl.) 19:57–64, 1991). The peripheral type receptor CCK-A is located in discrete brain nuclei and, in certain species, the spinal cord, and is also involved in gallbladder contraction and pancreatic enzyme secretion. The CCK-B/gastrin receptor is most abundant in the cerebral cortex, cerebellum, basal ganglia, and amygdala of the brain, as well as in parietal cells of the gastrointestinal tract. CCK-B receptor antagonists have been postulated to modulate anxiety, panic attacks, analgesia, and satiety (Ravard et al., Trends Pharmacol. Sci., 11:271–273, 1990; Singh et al., Proc. Natl. Acad. Sci. U.S.A., 88:1130–1133, 1991; Faris et al., Science, 219:310–312, 1983; Dourish et al., Eur.J.Pharmacol., 176:35–44, 1990; Wiertelak et al., Science, 256:830–833, 1992; Dourish et al., Science, 245:1509–1511, 1989).

SUMMARY OF THE INVENTION

Applicants have developed a systematic screening assay for identifying non-peptide agonists specific to peptide hormone receptors. The assay is based on applicants' recognition that a peptide hormone receptor having the capability of amplifying the intrinsic activity of a ligand is useful as a screening vehicle to identify receptor-specific agonists. In addition, a receptor with a signaling activity higher than the corresponding human wild-type basal level of signaling activity is especially useful for detecting a reduction in activity induced by an inverse agonist. In both cases, the receptor amplifies the signal generated when the ligand interacts with its receptor, relative to the signal generated when the ligand interacts with a human wild-type receptor. Thus, forms of a receptor with the ability to amplify receptor signaling are useful for efficiently screening positive and inverse non-peptide agonists to the corresponding human wild-type form of the receptor.

Accordingly, the invention features a method for determining whether a candidate compound is a non-peptide agonist of a peptide hormone receptor. In this method, a candidate compound is exposed to a form of the peptide hormone receptor which has a greater, or an enhanced, ability to amplify the intrinsic activity of a non-peptide agonist (hereafter an 'enhanced receptor'). The second messenger signaling activity of the enhanced receptor is measured in the presence of the candidate compound, and compared to the second messenger signaling activity of the enhanced receptor measured in the absence of the candidate compound. A change in second messenger signaling activity indicates that the candidate compound is an agonist. For example, an increase in second messenger signaling activity indicates that the compound is either a full or partial positive agonist; a decrease in second messenger signaling activity indicates that the compound is an inverse (also termed a 'negative') agonist.

By "intrinsic activity" is meant the ability of a ligand to activate a receptor, i.e., to act as an agonist. By 'amplify' is meant that the signal generated when the ligand interacts with the enhanced receptor is either higher for a positive agonist, or lower for an inverse agonist, than the signal produced when the same ligand interacts with a corresponding non-enhanced receptor, e.g., a wild-type human receptor. A 'non-enhanced receptor', for the purposes of this invention, is a wild-type human receptor for the peptide hormone of interest. By "corresponding" is meant the same type of peptide hormone receptor albeit in another form, e.g., a constitutively active mutant receptor. By way of example, the corresponding wild-type form of a constitutively active mutant CCK-B/gastrin receptor would be a wild-type CCK-B/gastrin receptor; the human CCK-B/gastrin receptor is the corresponding human form of the rat CCK-B/gastrin receptor.

Examples of enhanced receptors include synthetic mutant receptors, e.g., constitutively active mutant receptors; other mutant receptors with normal basal activity which amplify the intrinsic activity of a compound; naturally-occurring mutant receptors, e.g., those which cause a disease phenotype by virtue of their enhanced receptor activity, e.g., a naturally-occurring constitutively active receptor; and either constitutively active or wild-type non-human receptors, e.g., rat, mouse, mastomys, Xenopus, or canine receptors or hybrid variants thereof, which amplify an agonist signal to a greater extent than does the corresponding wild-type human receptor. An enhanced receptor may, but does not always, have a higher basal activity than the basal activity of a corresponding human wild-type receptor. Methods for measuring the activity of an enhanced receptor relative to the activity of a corresponding wild-type receptor are described and demonstrated below.

Examples of peptide hormone receptors within the scope of the invention include, but are not limited to, receptors specific for the following peptide hormones: amylin, angiotensin, bombesin, bradykinin, C5a anaphylatoxin, calcitonin, calcitonin-gene related peptide (CGRP), chemokines, cholecystokinin (CCK), endothelin, follicle stimulating hormone (FSH), formyl-methionyl peptides, galanin, gastrin, gastrin releasing peptide, glucagon, glucagon-like peptide 1, glycoprotein hormones, gonadotrophin-releasing hormone, leptin, luteinizing hormone (LH), melanocortins, neuropeptide Y, neurotensin, opioid, oxytocin, parathyroid hormone, secretin, somatostatin, tachykinins, thrombin, thyrotrophin, thyrotrophin releasing hormone, vasoactive intestinal polypeptide (VIP), and vasopressin. An enhanced receptor can further embrace a single transmembrane domain peptide hormone receptor, e.g., an insulin receptor.

An "agonist", as used herein, includes a positive agonist, e.g., a full or a partial positive agonist, or a negative agonist, i.e., an inverse agonist. An agonist is a chemical substance that combines with a receptor so as to initiate an activity of the receptor; for peptide hormone receptors, the agonist preferably alters a second messenger signaling activity. A positive agonist is a compound that enhances or increases the activity or second messenger signaling of a receptor. A "full agonist" refers to an agonist capable of activating the receptor to the maximum level of activity, e.g., a level of activity which is induced by a natural, i.e., an endogenous, peptide hormone. A "partial agonist" refers to a positive agonist with reduced intrinsic activity relative to a full agonist. As used herein, a "peptoid" is a peptide-derived partial agonist. An "inverse agonist", as used herein, has a negative intrinsic activity, and reduces the receptor's signaling activity relative to the signaling activity measured in the absence of the inverse agonist. A diagram explaining the difference between full and partial agonists, inverse agonists, and antagonists is shown in FIG. 1 (see also Milligan et al., *TIPS*, 16:10–13, 1995).

Examples of peptide hormone receptor specific peptide agonists and non-peptide antagonists useful in the screening assay of the invention are described below. Non-peptide ligands include, but are not limited to, the benzodiazepines, e.g., azabicyclo[3.2.2]nonane benzodiazepine (L-740,093; Castro Pineiro et al., WO 94/03437). L-740,093 S and L-740,093 R refer to the S-enantiomer and the R-enantiomer of L-740,093, respectively. Where the peptide hormone receptor is a CCK-A or CCK-B/gastrin receptor, useful peptide agonists include, but are not limited to, gastrin (e.g., sulphated ("gastrin II") or unsulphated ("gastrin I") forms of gastrin-17, or sulphated or unsulphated forms of gastrin-34), or cholecystokinin (CCK) (e.g., sulfated CCK-8 (CCK-8 s), unsulphated CCK-8 (CCK-8d), CCK-4, or pentagastrin (CCK-5)). Full agonists of the CCK-B/gastrin receptor include, but are not limited to, CCK-8s, and more preferably gastrin (gastrin I).

In contrast, an "antagonist", as used herein, refers to a chemical substance that inhibits the ability of an agonist to increase or decrease receptor activity. A 'full', or 'perfect' antagonist has no intrinsic activity, and no effect on the receptor's basal activity (FIG. 1). Peptide-derived antagonists are, for the purposes herein, considered to be non-peptide ligands.

The invention also features a method of isolating a form of a peptide hormone receptor suitable for detecting agonist activity of a non-peptide ligand. The method involves (a) exchanging a region of a functional domain of a first peptide hormone receptor with a corresponding region of a functional domain of a second peptide hormone receptor, the functional domain being selected from the group consisting of an intracellular loop and adjacent parts of a transmembrane domain; and (b) measuring the ability of the first peptide hormone receptor to amplify an agonist signal relative to a corresponding wild-type human receptor, a greater amplification in the first peptide hormone receptor would indicate that the first peptide hormone receptor is suitable for detecting agonist activity in a non-peptide ligand. The corresponding region can be between one and ten amino acids, e.g., a block of five to ten amino acids, or up to thirty or a hundred amino acids in length. The first and second peptide hormone receptors are preferably linked to different second messenger pathways. Those skilled in the art know which particular amino acids of the peptide hormone receptors are considered to be within extracellular, intracellular (cytoplasmic), or transmembrane regions of the receptor. For example, extracellular, intracellular, and transmembrane regions of the CCK-B/gastrin receptor are determined by sequence alignment with other receptors (FIG. 2), or by hydropathy analysis (Baldwin, *EMBO J.*, 12:1693–1703, 1993). Conformation receptor modelling is described further below.

Another method of isolating a form of a peptide hormone receptor suitable for detecting agonist activity in a non-peptide ligand involves (a) constructing a series of mutant forms of the receptor by replacing an original amino acid with another amino acid, i.e., a replacement amino acid; and (b) measuring the ability of the first peptide hormone receptor to amplify an agonist signal relative to the corresponding wild-type human receptor. An amplification in the first peptide hormone receptor would indicate that the first peptide hormone receptor is suitable for detecting agonist activity in a non-peptide ligand. The replaced amino acid can lie in an intracellular domain of the receptor or in a region of a transmembrane domain flanking an intracellular portion of the receptor, e.g., the intracellular domain-proximal half of the transmembrane domain, or within, e.g., 8 or 10 amino acids of the intracellular domain. The replacement amino acid can be of the same type in each of the mutant constructs, or various types of amino acids can be substituted at random. The replacement amino acid can be of the same or a different charge from the original amino acid, e.g., a negative amino acid can be exchanged for a positive amino acid, a positive amino acid can be exchanged for a negative amino acid, or a positive or negative amino acid can be exchanged for a neutral amino acid. Preferably, the replacement amino acid is glutamine, glutamic acid, aspartic acid, or serine.

Other terms used in the various embodiments of the invention will be understood from the following definitions. For example, by a "peptide hormone" is meant a polypeptide that interacts with a target cell by contacting an extracellular receptor, i.e., a "peptide hormone receptor". A "peptide" is used loosely herein to refer to a molecule comprised of amino acid residues that are connected to each other by peptide bonds. A "mutant receptor" is understood to be a form of the receptor in which one or more amino acid residues in the predominant receptor occurring in nature, e.g., in a naturally-occurring wild-type receptor, have been either deleted or replaced with a different type of amino acid residue. By a "constitutively active receptor" is meant a receptor with a higher basal activity level than the corresponding wild-type receptor, where activity means the spontaneous ability of a receptor to signal in the absence of further activation by a positive agonist. The basal activity of a constitutively active receptor can also be decreased by an inverse agonist. A "naturally-occurring" receptor refers to a form or sequence of the receptor as it exists in an animal, or to a form of the receptor that is synonymous with the sequence known to those skilled in the art as the "wild-type" sequence. Those skilled in the art will understand a "wild-type" receptor to refer to the conventionally accepted "wild-type" amino acid consensus sequence of the receptor, or to a "naturally-occurring" receptor with normal physiological patterns of ligand binding and signaling. A "second messenger signaling activity" refers to production of an intracellular stimulus (including, but not limited to, cAMP, cGMP, ppGpp, inositol phosphate, or calcium ion) in response to activation of the receptor, or to activation of a protein in response to receptor activation, including but not limited to a kinase, a phosphatase, or to activation or inhibition of a membrane channel.

"Sequence identity," as used herein, refers to the subunit sequence similarity between two nucleic acid or polypeptide molecules. When a given position in both of the two molecules is occupied by the same nucleotide or amino acid residue, e.g., if a given position (as determined by conventionally known methods of sequence alignment) in each of two polypeptides is occupied by serine, then they are identical at that position. The identity between two sequences is a direct function of the number of matching or identical positions, e.g., if 90% of the positions in two polypeptide sequences are identical, e.g., 9 of 10, are matched, the two sequences share 90% sequence identity. Methods of sequence analysis and alignment for the purpose of comparing the sequence identity of two comparison sequences are well known by those skilled in the art. "Biological activity", as used herein, refers to the ability of a peptide hormone receptor to bind to a ligand, e.g., an agonist or an antagonist and to induce signaling.

The invention provides an efficient and rapid assay for identifying non-peptide agonists that interact with a peptide hormone receptor. The newly identified agonists can serve as therapeutics, or as lead compounds for further pharmaceutical research. Systematic chemical modifications can be made; their effects can be functionally assessed in enhanced receptors according to the method of the invention. By following such a development strategy the intrinsic activity of new agonists is optimized so as to provide useful therapeutics against diseases involving a peptide-hormone receptor.

Also embraced are the various mutant peptide hormone receptors disclosed herein, and their respective nucleic acid coding sequences. Plasmid manipulation, storage, and cell transformation are performed by methods known to those of ordinary skill in the art. See, e.g., Ausubel et al. (eds.), *Current Protocols in Molecular Biology*, John Wiley & Sons, Inc., NY. 1988, 1995.

Other features and advantages of the invention will be apparent from the following detailed description and from the claims.

DETAILED DESCRIPTION

We first briefly describe the drawings.

DRAWINGS

FIG. 1 is a schematic diagram showing the relationship between a full or partial agonist, an inverse agonist, and an antagonist.

FIG. 2 is an illustration showing a multiple alignment of cloned CCK receptor deduced amino acid sequences mastomys CCK-B (SEQ ID NO: 1), rat CCK-B (SEQ ID NO: 2), human CCK-B (SEQ ID NO: 3), canine CCK-B (SEQ ID NO: 4), human CCK-A (SEQ ID NO: 5), rat CCK-A (SEQ ID NO: 6), and Xenopus CCK-XL (SEQ ID NO: 7). 'A' marks the position in the hCCK-A receptor where an E to Q substitution results in an increase in PD 135,158 intrinsic activity without increasing basal receptor activity. 'B' marks the position in the hCCK-B receptor where an L to either S or E substitution results in an increase in basal activity. The corresponding L to S in the hCCK-A receptor does not result in an increase in basal activity. 'C' marks the position in the hCCK-B receptor where a V to E substitution results in an increase in basal activity. The corresponding I to E substitution in the human CCK-A receptor does not result in an increase in basal activity. The numbering shown is generic; each receptor is different based on deletions or insertions.

FIG. 3 is a bar graph showing that the intrinsic activity of peptide, peptide-derived and non-peptide ligands at the wild-type CCK-B/gastrin receptor (top panel) is amplified in a constitutively active receptor mutant (bottom panel).

FIG. 4 is an illustration of inositol phosphate production by the non-peptide agonist L-740,093. Top panel: L-740,093 S stimulated inositol phosphate production in COS-7 cells expressing a constitutively active human CCK-B/gastrin receptor. Bottom panel: YM022 antagonizes the partial agonist activity induced by 10 nM L-740,093-S.

FIG. 5 is an illustration of the inositol phosphate production of the non-peptide agonist L-740,093-R. Top panel: L-740,093 R inhibits basal inositol phosphate production in COS-7 cells expressing a constitutively active human CCK-B/gastrin receptor. Bottom panel: The inverse agonist activity induced by 10 nM L-740,093 R is partially abolished by YM022 in a concentration-dependent fashion.

Recent drug development efforts have led to the discovery of many small molecules which competitively block G-protein coupled peptide hormone receptors. In contrast, very few non-peptide ligands have been identified which activate this family of receptors. Here, Applicants demonstrate that chemical modifications of known non-peptide ligands for the CCK-B/gastrin receptor can interconvert small molecules from antagonists to either positive agonists or to inverse agonists. Changes in the intrinsic activity of the ligand resulting from such modifications were detectable because Applicants designed a screening assay which employed a constitutively active mutant of the human CCK-B/gastrin receptor ($^{325}$L→E). Several peptide, 'peptoid' and benzodiazepine-based non-peptide ligands were tested in this assay, and evaluated for their abilities to activate the recombinant wild-type or constitutively active mutant receptor, respectively. Whereas full agonists had similar signaling efficacy in both receptors when compared to the intrinsic activity of the peptide agonist CCK-8s, the effect of ligands with lesser intrinsic activity was logarithmically amplified by the constitutively active mutant receptor. The prototype benzodiazepine-derived non-peptide 'antagonist' L-365,260 barely increased basal activity of the wild-type CCK-B/gastrin receptor, but was identified as a partial agonist using the $^{325}$L→E mutant. Minor chemical modification of L-365,260 resulted in compounds which were pure antagonists (YM022), partial agonists (L-740,093 S) or inverse agonists (L-740,093 R). The drug discovery process for novel non-peptide agonists, including those with reverse intrinsic activity, should be guided by using enhanced receptors, e.g., constitutively active mutant receptors, in the screening assay so as to expedite identification of potential lead compounds.

I. Working Example:

The following example demonstrates the usefulness of an enhanced peptide hormone receptor to screen for non-peptide agonists.

Using a constitutively active mutant of the human CCK-B/gastrin receptor it was discovered that several benzodiazepine-based putative non-peptide 'antagonists' had detectable intrinsic activity when binding to this receptor.

Figure 3:
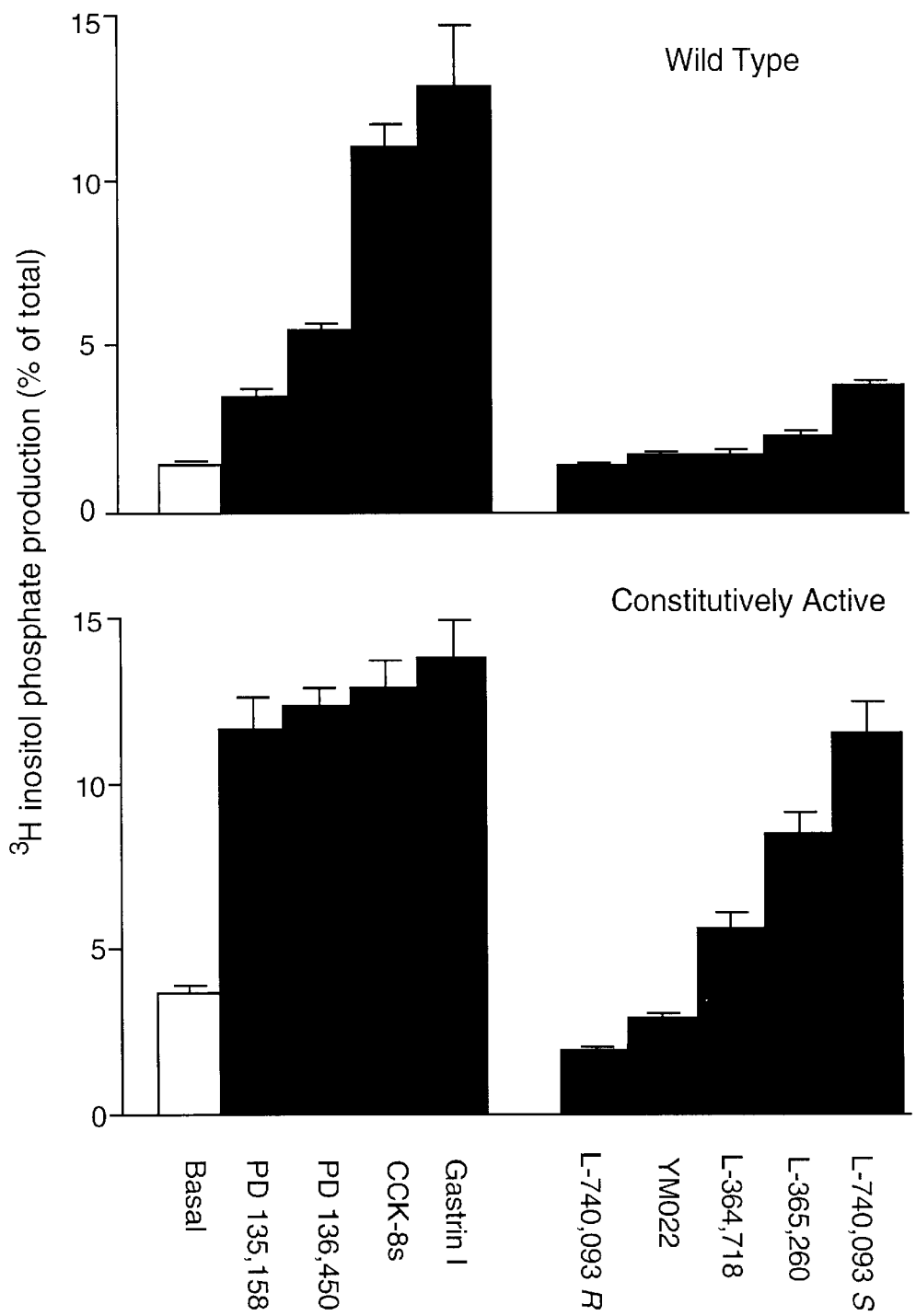

The constitutively active CCK-B/gastrin receptor mutant $^{325}$L→E was transiently overexpressed in COS-7 cells. The fact that it was constitutively active was evident from ligand-independent production of inositol phosphate; the wild-type receptor, in contrast, exhibits only ligand-dependent inositol phosphate production. Both mutant and the wild-type receptors induced similar inositol phosphate production when maximally stimulated with the peptide agonists CCK-8s or gastrin I (FIG. 3). In contrast, only the mutant CCK-B/gastrin receptor allowed detection of the different degrees of intrinsic activities of three benzodiazepine-derived compounds, L-740,093 R, YM022 and L-365,260. Each of these compounds were previously considered prototype non-peptide antagonists of the wild-type CCK-B/gastrin receptor (Castro Pineiro et al., WO 94/03437; Lotti et al., *Eur. J. Pharmacol.*, 162:273–280, 1989; Nashida et al., *J. Pharmacol. Exp. Ther.*, 270:1256–61, 1994; Nashida et al., *J. Pharmacol. Exp. Ther.*, 269:725–31, 1994).

The non-peptide compound L-365,260 had 62% efficacy when compared to the full agonist CCK-8s, and was on that basis identified as a partial agonist in the $^{325}$L→E constitutively active mutant receptor (FIG. 3, right section). In fact, close re-examination of this compound's function in the wild-type CCK-B/gastrin receptor also revealed a barely detectable, yet significant, increase in inositol phosphate production that had not been seen with the other non-peptide compounds.

From the above results it was concluded that minor changes in the chemical groups attached to the benzodiazepine backbone can result in marked alterations in intrinsic activity of small non-peptide compounds. The stereochemistry of benzodiazepine-derived CCK receptor ligands is another feature which can alter binding affinity as well as receptor selectivity (Showell et al. *J. Med. Chem.* 37:719–721, 1994).

The following additional observations confirmed that differences in ligand stereochemistry determine the functional properties of the CCK-B/gastrin receptor specific compounds. For example, it was noted that L-740,093 S was almost a full agonist in the $^{325}$ L→E CCK-B/gastrin receptor mutant (FIG. 3). When tested with the human wild-type CCK-B/gastrin receptor, L-740,093 S functions as a partial agonist (25% efficacy compared with CCK-8s). As such, L-740,093 S is the first known non-peptide agonist for the CCK-B/gastrin receptor. The mirror image of L-740,093 S, L-740,093 R, has properties opposite to those of the S enantiomer. L-740,093 R reduces the basal activity of the constitutively active receptor almost to wild-type levels.

To confirm the functional classification of CCK-B/gastrin receptor non-peptide ligands, basic pharmacologic principles were tested to determine whether they applied to interactions between the CCK-B/gastrin receptor and the benzodiazepine-derived agonists and antagonists. Of the compounds tested, YM022 came closest to being a 'perfect' antagonist, with almost no intrinsic activity on either the wild-type or the constitutively active CCK-B/gastrin receptor. In both the wild-type and the constitutively active receptors, YM022 blocked CCK-8s induced inositol phosphate production with almost identical affinity, reflected by similar pA2 values (9.78 and 9.37, respectively). Consistent with the functional classification of L-740,093 S as a non-peptide agonist, the inositol phosphate production induced by this compound could be blocked by YM022 (pA2=9.54; FIG. 4). YM022 was also able to attenuate the inverse agonist activity of L-740,093 R on the constitutively active CCK-B/gastrin receptor (FIG. 5). In a concentration-dependent manner, YM022 partially restored basal activity to the constitutively active receptor which had been inhibited by 20 nM L-740,093 R. The fact that basal activity was not restored completely is explained by the fact that YM022 itself is a weak inverse agonist in this mutant rather than a pure receptor antagonist.

The pA2 value measures the functional affinity of a competitive antagonist. In contrast to $IC_{50}$ values (50% inhibitory concentration), $pA_2$ values are independent of which agonist concentrations are used to measure antagonist affinities. Ideally, $pA_2$ values should also be independent of what specific agonist compounds are tested to assess antagonist affinities. The pA2 value is defined as the negative logarithm of the specific antagonist concentration which shifts the agonist concentration-response curve by a factor of two to the right. In other words, in the presence of a given antagonist concentration, one would need twice as much agonist as would be required in the absence of antagonist to induce the same effect. $pA_2$ values of competitive antagonists are typically assessed by Schift plots, but can also be measured by simplified 'null' methods (Lazareno et al., *Trends in Pharmacol. Sci.*, 14:237–239, 1993).

In addition to non-peptide ligands, the constitutively active mutant receptor amplified the intrinsic activity of peptide-derived partial agonists ('peptoids'; Horwell et al., *Eur. J. Med. Chem.*, 30 Suppl.:537S–550S, 1995; Horwell et al., *J. Med. Chem.*, 34:404–14, 1991). The peptoids used in the following experiments were derived from sequential modification of CCK-4. Two prototype 'peptoid' compounds, PD 135,158 and PD 136,450, were converted from partial agonists in the wild-type to almost full agonists in the constitutively active CCK-B/gastrin receptor. Thus, peptide-derived as well as non-peptide compounds have increased efficacy on the constitutively active versus the wild-type CCK-B/gastrin receptor. Despite these marked alterations in efficacy, the ratio of wild-type versus mutant receptor affinities, as determined by $^{125}$I-CCK-8 competition binding experiments, fell within a two-fold range (Table 1 A). There was no apparent correlation between the intrinsic activity of CCK-B/gastrin receptor ligands and potency shifts between the wild-type and the constitutively active receptors (Table 1 B).

Figure 6:
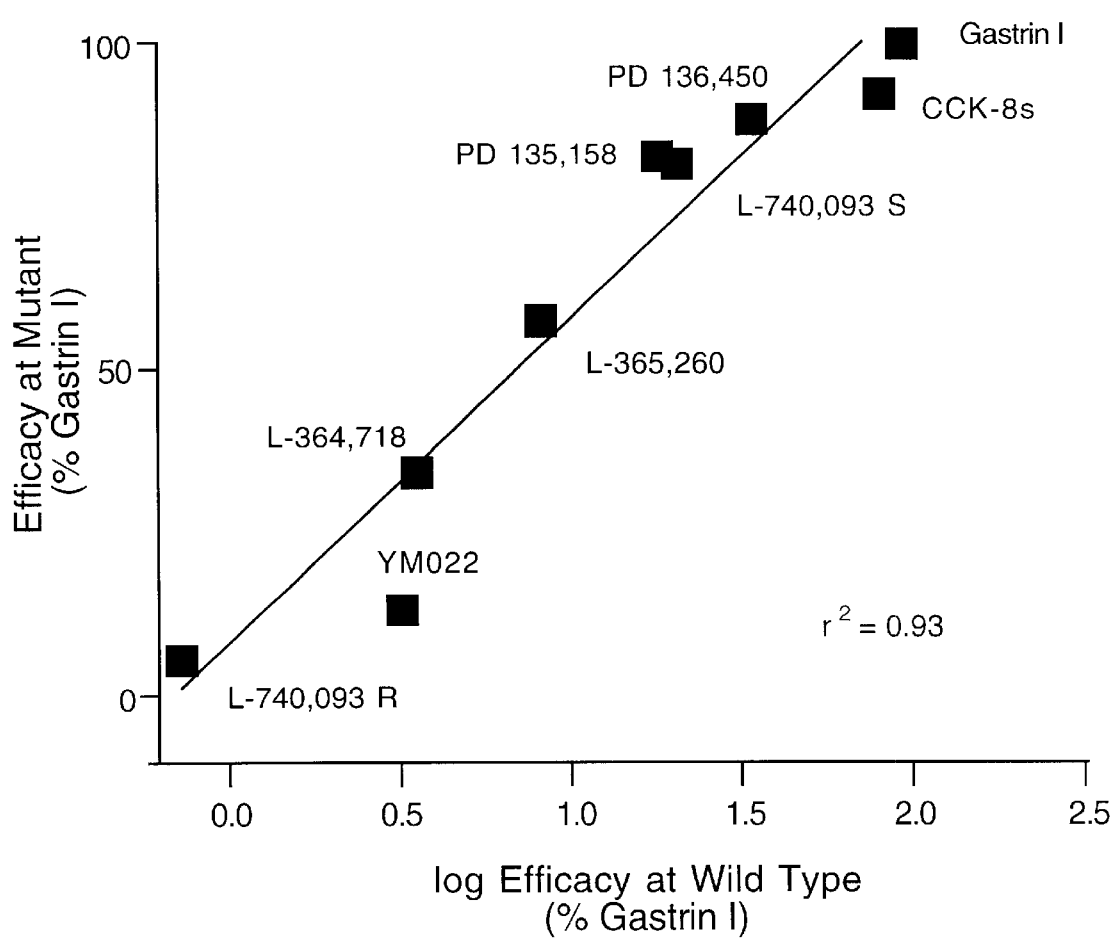
FIG. 6 is a comparison of intrinsic activities of CCK-B/gastrin receptor ligands utilizing the wild-type and the constitutively active receptors. Values for all compounds follow a logarithmic-linear correlation (r2=0.93).

Precedent with the constitutively active CCK-B/gastrin receptor illustrates a new strategy using mutant receptors as a 'magnifying glass' to screen for non-peptide leads with some degree of intrinsic activity. It should be noted that the constitutively active $^{325}$L→E mutant reliably predicted the intrinsic activity that a compound would possess when stimulating the wild-type receptor (FIG. 6). This was true over the spectrum of peptide, 'peptoid', and non-peptide ligands tested.

The intrinsic activity (percent maximal stimulation of inositol phosphate formation) of all compounds was tested at concentrations that were at least 100-fold higher than the corresponding receptor affinities.

The intrinsic activity of L-740,093 S was comparable to that observed for the 'peptoid' ligand PD 135,158, a compound that has been recently demonstrated to be a partial agonist in vivo (Ding et al., Gastroenterology, 109:1181–87, 1995).

TABLE 1

A) $^{125}$I CCK-8 binding affinities of tested ligands

| Compound | Wild-type receptor Ki(nM) | $^{325}$L→E Mutant Ki(nM) | Ratio (Wild-type/Mutant) |
|---|---|---|---|
| Gastrin I | 1.35 ± 0.28 | 0.80 ± 0.16 | 1.69 |
| CCK-8s | 0.12 ± 0.01 | 0.07 ± 0.01 | 1.71 |
| PD 135,158 | 2.25 ± 0.61 | 1.01 ± 0.19 | 2.23 |
| PD 136,450 | 0.99 ± 0.1 | 0.59 ± 0.12 | 1.68 |
| L-740,093 R | 0.19 ± 0.02 | 0.18 ± 0.04 | 1.06 |
| YM022 | 0.07 ± 0.01 | 0.08 ± 0.01 | 0.88 |
| L-364,718 | 150 ± 42 | 170 ± 34 | 0.88 |
| L-365,158 | 7.16 ± 0.87 | 7.83 ± 1.51 | 0.91 |
| L-740,093 S | 19.5 ± 1.5 | 16 ± 1.4 | 1.22 |

B) Signaling potencies of tested ligands

| Compound | Wild-type receptor IC50(nM) 95% C.I. | $^{325}$L→E Mutant IC50(nM) 95% C.I. | Ratio (Wild-type/Mutant) |
|---|---|---|---|
| Gastrin I | 0.24 (0.12–0.48) | 0.20 (0.06–0.69) | 1.20 |
| CCK-8s | 0.14 (0.11–0.19) | 0.15 (0.08–0.30) | 0.93 |
| PD 135,158 | 1.05 (0.29–3.83) | 1.01 (0.21–4.80) | 1.04 |
| PD 136,450 | 0.36 (0.04–3.35) | 0.58 (0.23–1.46) | 0.62 |

II. Receptor Binding and Activity Assays:

A. Receptor Binding Assays:

The binding of a ligand to a CCK receptor, e.g., the CCK-A or the CCK-B/gastrin receptor, can be measured according to the following example. In this example, the binding affinity of a ligand to the human CCK-B/gastrin receptor is measured.

COS-7 cells ($1.5 \times 10^6$) were plated in 10-cm culture dishes (Nunc) and grown in Dulbecco's modified Eagle's medium containing 10% fetal calf serum in a 5% $CO_2$, 95% air incubator at 37° C. After an overnight incubation, cells were transfected (Pacholczyk et al., Nature 350:350–354, 1991) with 5–7 µg of a pcDNA I expression vector containing hCCKB (HCCKB-pcDNA I). Twenty-four hours after transfection cells were split into 24-well dishes ($2 \times 10^4$ cells/well) (Costar). After an additional 24 hours, competition binding experiments were performed in Hank's buffer supplemented with 25 mM phenylmethylsulfonyl fluoride (PMSF). Twenty pM of $^{125}$I CCK-8 (DuPont-New England Nuclear) was used as radioligand. Equilibrium binding occurred after incubation for 80 min. at 37° C. Cell monolayers were then washed three times, hydrolyzed in 1 N NaOH, and the amount of radioactivity to the receptor was quantified. Unlabeled agonists (e.g., CCK-8s, unsulphated CCK-8 (CCK-8 us), gastrin I, CCK-4 (Peninsula)) and antagonists (L364,718 and L365,260 (Merck)) were tested over the concentration range of 0.1 pM to 10 µM. All binding experiments were repeated three to five times.

The competition data were analyzed using computer software which is specifically designed for the purpose of radioligand binding assays (Inplot 4.0, GraphPad, San Diego, Calif.). Analyses of competition and saturation binding data can also be performed using computerized non-linear curve fitting (McPherson, G. A., J Pharmacol Methods, 14:213–28, 1985).

The affinities of all agonists and antagonists were confirmed by repeating the above assay using Chinese hamster ovary (CHO) cells stably transfected with human CCK-B/gastrin receptor cDNA. This CHO cell line was established by transfecting a hCCKB-pcDNAI Neo expression vector (Invitrogen) into CHO cells using a standard lipofection protocol (Bethesda Research Laboratories) followed by G418 selection.

Where binding parameters are determined in isolated plasma membranes, binding can be performed, e.g., for 60 min. at 22° C. (Kopin et al., Proc. Natl. Acad. Sci. USA, 89:3605–09, 1992). Separation of bound and free radioligand can be achieved by receptor-binding filtermat filtration (Klueppelberg, U. G., et al., 1989, Biochemistry 28:3463–8).

In order to compare the binding specificity of CCKB/gastrin mutant receptors of the invention with the binding specificity typical of wild-type CCK-B/gastrin receptors see Matsumoto et al. (Am J Physiol., 252:G143–G147, 1987) and Lee et al. (J. Biol. Chem., 268(11):8164–69, 1993).

Figure 7A:
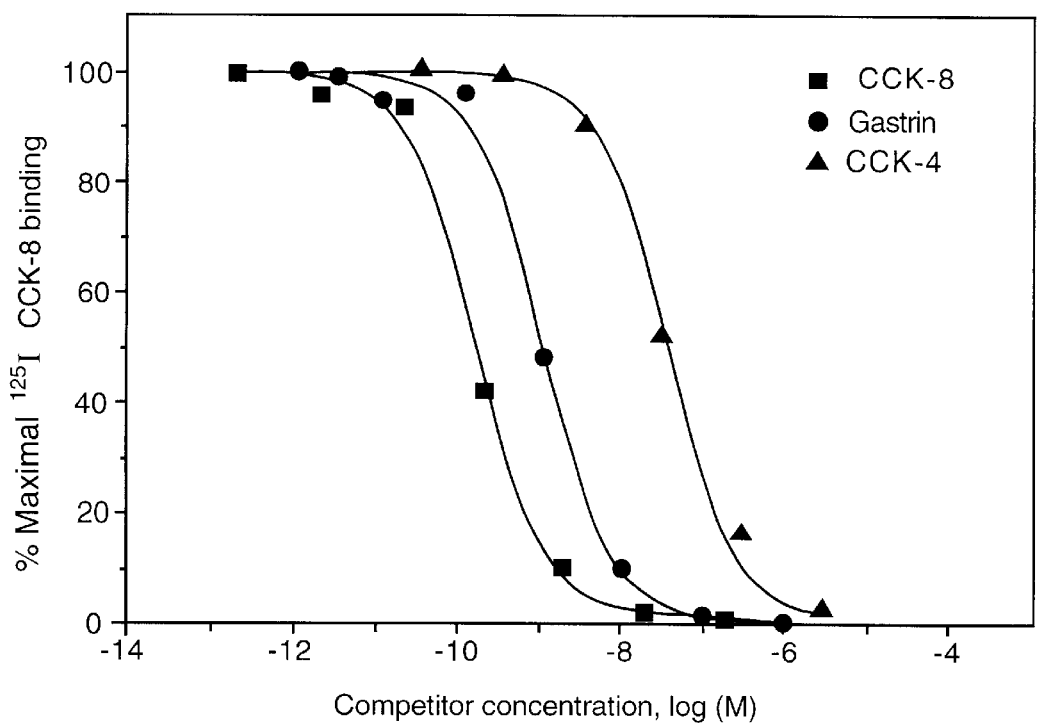
FIG. 7 is a competition binding curve showing the extent of $^{125}$I-CCK-8 receptor binding. Binding of $^{125}$I-CCK-8 to COS-7 cells, transiently transfected with hCCK-B-pcDNAI is shown in the presence of increasing concentrations of CCK-8, gastrin I, and CCK-4 (part A) and L-364,718 and L-365,260 (part B).
Figure 7B:
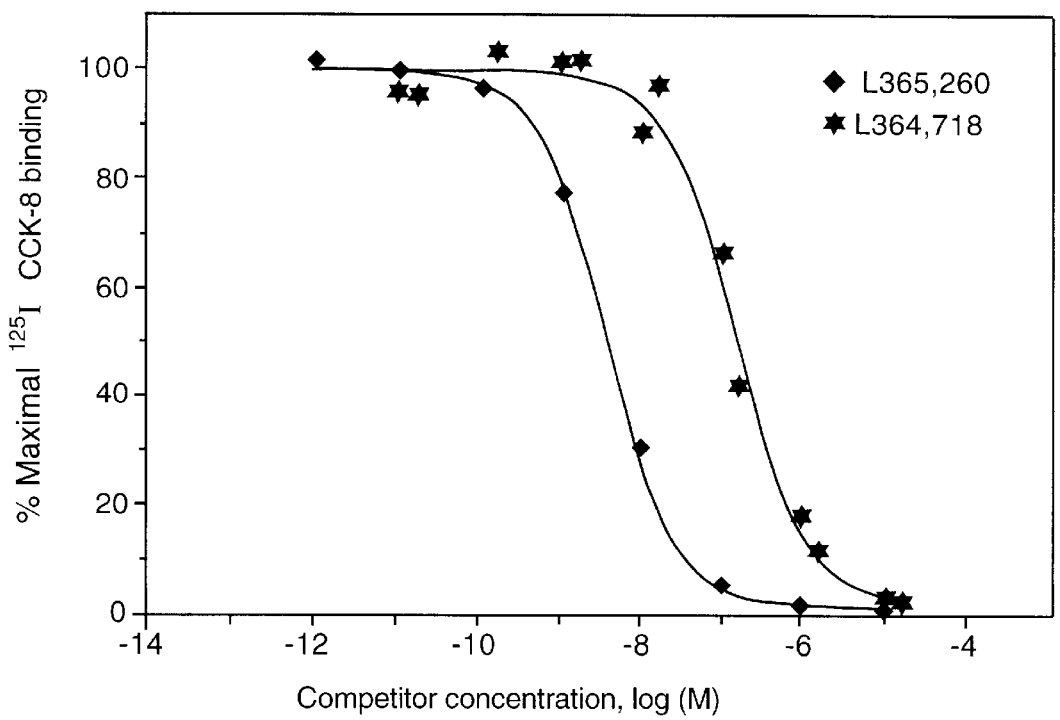

Comparison of binding affinity to that of a wild-type human CCK-B receptor: A base line value for binding of a radiolabelled ligand to a human wild-type receptor, e.g., the human CCK-B/gastrin receptor was determined (see Lee et al., J. Biol. Chem., 268(11):8164–69, 1993). Agonist affinities of the human brain CCK-B/gastrin receptor expressed in COS-7 cells were characterized (FIG. 7). The structurally related agonists CCK-8s, gastrin I, and CCK-4 all competed in a concentration-dependent manner for binding of $^{125}$I-CCK-8 to COS-7 cells expressing the recombinant receptor. The calculated $IC_{50}$ values for CCK-8s, gastrin I, and CCK-4 are 0.14, 0.94, and 32 nM respectively (FIG. 7, part A). Similar $^{125}$I-CCK-8 competition curves were assessed with L-364,718 and L365,260 (FIG. 7, part B), and revealed $IC_{50}$ values of 145 and 3.8 nM, respectively. Untransfected cells showed no displaceable binding.

B. Receptor Signaling Activity Assays:

Binding of an agonist to a CCK receptor elicits an increase in the intracellular calcium concentration and in phosphatidylinositol hydrolysis.

Measurement of $[Ca^{2+}]$: Forty-eight hours after transfection with hCCKB-pcDNAI, COS-7 cells were loaded with the $Ca^{2+}$ fluorophore fura-2 in modified Krebs-Ringer bicarbonate buffer. Changes in the fluorescence emission ratios (340:380 nm) after stimulation of cells with $10^{-7}$ M CCK-8s or $10^{-6}$ M gastrin I were measured as previously described (Rajan et al., Diabetes, 38:874–80, 1989). Extracellular calcium can be chelated with EGTA (2.5 mM) to confirm that a gastrin-induced increase in $[Ca^{2+}]$ originates primarily from intracellular $[Ca^{2+}]$ pools.

Measurement of Inositol phosphate Metabolites: COS-7 cells transfected with hCCKB-pcDNAI were cultured in inositol-free Dulbecco's modified Eagle's medium (DMEM, GIBCO) which was supplemented with 10 µCi/ml [$^3$H]myo-inositol (ARC) for 24 hours prior to analysis. After 1 hour of equilibration in modified Krebs-Ringer bicarbonate, the cells were stimulated with $10^{-7}$M CCK-8s for 10 seconds and harvested in methanol-HCl. The aqueous phase was extracted with chloroform, lyophilized, and analyzed for inositol 1,4,5-triphosphate (Ins-1,3,4,5-$P_3$) and inositol 1,3, 4,5-tetrakisphosphate (Ins-1,3,4,5-$P_4$) by strong anion-exchange high performance liquid chromatography (Auger et al., Cell, 57:167–75, 1989).

Figure 8A:
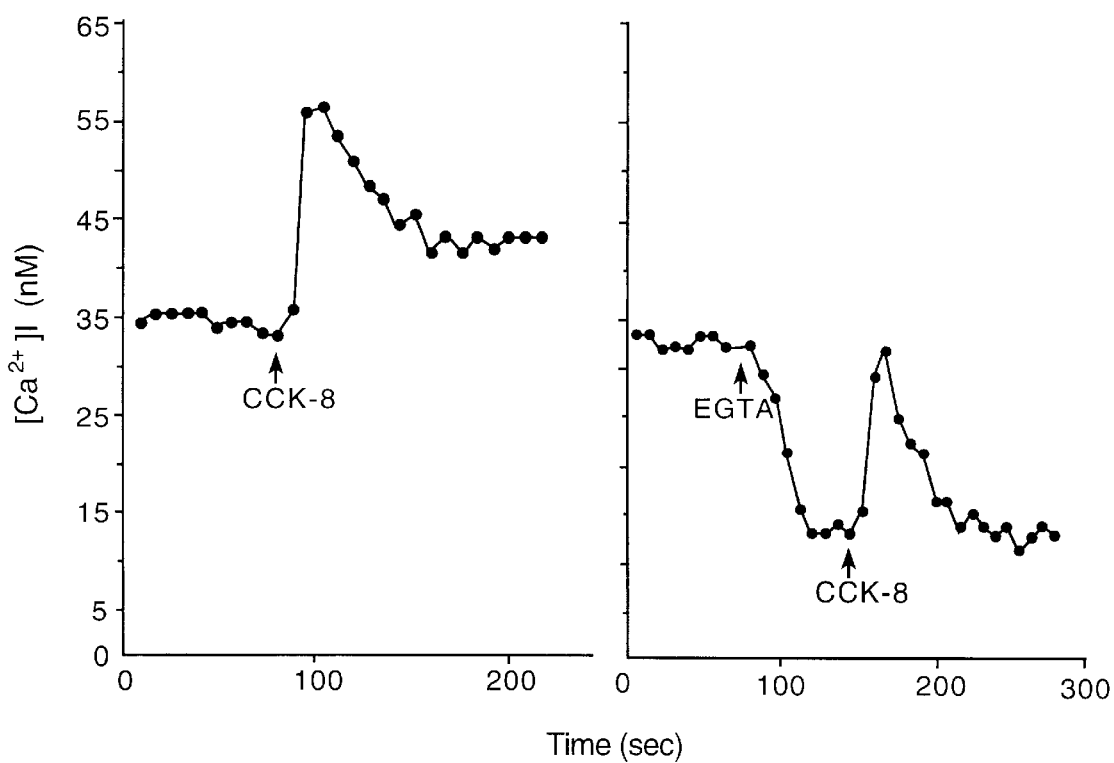
FIG. 8 is a graph showing second messenger signaling (i.e., mobilization of intracellular calcium) in COS-7 cells that express the recombinant human brain CCK-B receptor with (part A, left panel) and without (part A, right panel) the addition of the calcium chelator, EGTA. This is paralleled by an increased production of inositol phosphate (part B).
Figure 8B:
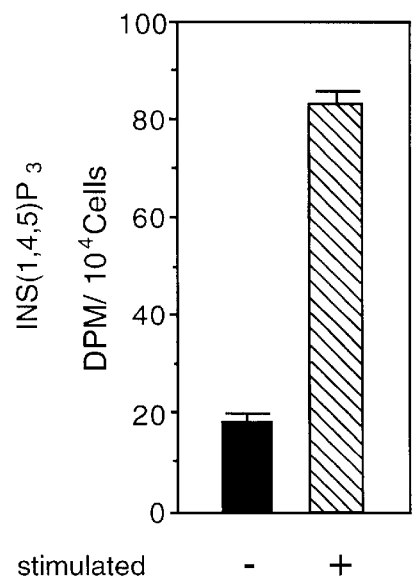

Comparison of signaling activity to that of a wild-type human CCK-B receptor: A baseline level of human wild-type CCK-B receptor second messenger signaling activity was measured in response to CCK-8s stimulation of COS-7 cells expressing the receptor (FIG. 8; see Lee et al., J. *Biol. Chem.*, 268(11):8164–69, 1993). CCK-8s ($10^{-7}$M) triggered a marked increase in free cytosolic calcium, $[ca^{2+}]_i$ (FIG. 8, part A, left panel). There was no change in free cytosolic calcium in cells transfected with the empty expression vector, pcDNAI. After chelation of extracellular calcium (1.5 mM $Ca^{2+}$ in the buffer) by 2.5 mM EGTA, addition of CCK-8s ($10^{-7}$ M) still transiently increased $[Ca^{2+}]_i$ (FIG. 8, part A right panel), suggesting that the initial peak of the CCK-induced increase in $[Ca^{2+}]_i$ originated primarily from intracellular $Ca^{2+}$ pools. The arrows indicate the addition of CCK-8s (0.1 $\mu$M) or EGTA (2.5 mM). The pattern of $[Ca^{2+}]_i$ response suggests that the binding of CCK-8s to the recombinant receptor triggers intracellular signaling through activation of phospholipase C. This was confirmed by measurement of inositol phosphate metabolites in hCCKB-pcDNA I-transfected COS-7 cells 10 seconds after CCK-8s stimulation (FIG. 8, part B). This time point was chosen because it immediately precedes the CCK-8-induced $[Ca^{2+}]_i$ peak. CCK-8s ($10^{-7}$M) increased the level of Ins-1,4,5-$P_3$ by 453% over control, unstimulated hCCKB-pcDNA I-transfected COS-7 cells (n=3, p<0.001). The level of Ins-1,3,4,5-$P_4$, an immediate metabolite of Ins-1,4,5,-P3, also increased by 186% over control (n=3, p<0.01).

A simplified method for measuring total inositol phosphate content: While the above method specifically assesses Ins(1,4,5)$P_3$ content, a simplified screening method can be used to test for the total concentration of inositol phosphate; the simplified method does not distinguish between specific isoforms. (This method was used to measure inositol phosphate generation for the experiments shown in FIGS. 3, 4, 5, 6, and 10.)

COS-7 cells transfected with receptor cDNA-pcDNAI were cultured in inositol-free, serum-free Dulbecco's modified Eagle's medium (DMEM, GIBCO), supplemented with 3 $\mu$Ci/ml $^3$ H-myo-inositol (NEN, 45–80 Ci/mmol), for 18 hours prior to analysis. The cells were then washed twice with DMEM/10 mM LiCl$_2$ and twice with phosphate-buffered saline/10 mM LiCl$_2$. After stimulation with putative agonists in phosphate-buffered saline 10/mM LiCl$_2$ for 30 minutes at 37° C., cells were scraped in ice-cold methanol. Lipids were extracted with chloroform (Pfeiffer et al., *FEBS Lett.*, 204:352–356, 1986). The upper phase was analyzed for inositol phosphates by strong anion exchange chromatography, using Dowex 1-X8 columns (BIORAD) and differential elution with water/60 mM ammonium fornate/2 M ammonium fornate. Eluted radioactivity was measured by liquid scintillation counting, and inositol phosphate content was expressed as a percentage of total $^3$H-radioactivity applied to the columns.

Further information on the second messenger pathways linked to the native parietal cell gastrin receptor can be obtained in the following references: Muallem, S. et al., 1984, *Biochim Biophys Acta* 805:181–5; Chew, C. S. et al., 1986, *Biochim Biophys Acta* 888:116–25; Roche, S. et al., 1991, *FEBS Letts.*, 282:147–51.

In addition to inositol phosphate production, second messenger signaling activity can be measured according to, e.g., cAMP, cGMP, ppGpp, or calcium ion production, or using as indicators, e.g., intracellular pH, pH-sensitive dyes, or expression of a reporter gene, e.g., a luciferase gene, or measuring channel activity or cell depolarization or hyperpolarization by electrophysiological techniques.

III. Suitable Peptide Hormone Receptors with the Ability to Amplify the Intrinsic Activity of a Non-peptide Agonist:

The screening assay of the invention can be performed using peptide hormone receptors that have a higher activity than the corresponding human wild-type receptor. An enhanced basal activity amplifies the intrinsic activity of ligands, and is useful for detecting either activation of the receptor by a partial agonist, or inhibition by an inverse agonist. Receptors that do not have an enhanced basal activity relative to the corresponding wild-type receptor, but still amplify the intrinsic activity of a partial agonist, are also useful.

Examples of peptide hormone receptors that are useful for screening non-peptide agonists include various forms of the receptors that interact with the following peptide hormones (along with references for their respective wild-type amino acid sequences): amylin, angiotensin, bombesin, bradykinin, C5a anaphylatoxin, calcitonin, calcitonin-gene related peptide (CGRP), chemokines, cholecystokinin (CCK), endothelin, follicle stimulating hormone (FSH), formyl-methionyl peptides, galanin, gastrin, gastrin releasing peptide, glucagon, glucagon-like peptide 1, glycoprotein hormones, gonadotrophin-releasing hormone, leptin, luteinizing hormone (LH), melanocortins, neuropeptide Y, neurotensin, opioid, oxytocin, parathyroid hormone, secretin, somatostatin, tachykinins, thrombin, thyrotrophin, thyrotrophin releasing hormone, vasoactive intestinal polypeptide (VIP), and vasopressin. An enhanced receptor can further embrace a single transmembrane domain peptide hormone receptor, e.g., an insulin receptor. The wild-type amino acid sequences of the above peptide hormone receptors is available in, and/or referenced in, Watson and Arkinstall, *The G-Protein Linked Receptor*, Academic Press, NY., 1994.

Forms of a peptide hormone receptor that are capable of amplifying the intrinsic activity of an agonist include, but are not limited to, the following forms of receptors:

1. Mutant peptide hormone receptors that are capable of amplifying the intrinsic activity of partial agonists.

An example is given of a mutant human CCK-A receptor that enhances the intrinsic activity of the partial 'peptoid' agonist PD 135,158, yet causes no apparent increase in agonist-independent basal receptor activity, is the mutant CCK-A receptor pMHA35. pMHA35 was made by replacing amino acids 138-ERY-140 of the human wild-type CCK-A receptor with QRY in the vector pcDNAI. (See FIG. 2 for an illustration of the wild-type CCK-A receptor amino acid sequence.)

2. CCK-A receptors in which one or more of residues $^{138}$E, $^{305}$L, and $^{312}$I are replaced with any other amino acid residue, e.g., a serine, aspartic acid, glutamine, or glutamic acid residue.

3. CCK-B/gastrin receptors in which one or more of residues $^{151}$E, $^{325}$L, and $^{332}$V are replaced with any other amino acid residue, e.g., a serine, aspartic acid, glutamine, or glutamic acid residue.

4. Naturally-Occurring Mutant Receptors, including but not limited to naturally-occurring constitutively active mutant receptors, that are associated with a disease or other adverse phenotype, e.g., a phenotype that results from a constitutively active naturally-occurring mutant receptor. Examples include, but are not limited to, the following peptide hormone receptors:

a) Point mutations in the luteinizing hormone (LH) receptor gene are responsible for some incidences of precocious puberty. Mutant receptors of the invention can be constructed by altering the following amino acid residues of the LH receptor: the alanine residue at position 568 to another amino acid, e.g., to a valine (Latronico et al., *J. Clin. Endo. & Meta.*, 80(8):2490–94, 1995); the asparagine residue at position 578 to another amino acid, e.g., to a glycine or a tyrosine (Kosugi et al., *Human Mol. Genet.*, 4(2):183–88, 1995; Laue et al., *Proc. Natl. Acad. Sci. USA*, 92(6):1906–10, 1995); the Met residue at position 571 to another amino acid, e.g., to an Ile, or the Thr residue at 577 to another amino acid residue, e.g., to an Ile (Kosugi et al., supra; Laue et al. supra); the Ile residue at position 542 to another amino acid, the Asp residue at position 564 to another amino acid, the Cys residue at position 581 to another amino acid, or the Asp residue at position 578 to another amino acid (Laue et al., supra); amino acid residues within transmembrane helices 5 or 6, e.g., in the intracellular domain-proximal portion of transmembrane helix 6, or in intracellular loop 3 (Laue et al. supra).

Also embraced are mutations at the corresponding residues of the follicle stimulating hormone (FSH) receptor and the thyroid stimulating hormone (TSH) receptor (Latronico et al., supra).

b) A naturally-occurring constitutively active parathyroid (PTH) receptor results from a His to Arg substitution at conserved position 223 (Schipani et al., *Science*, 268:98–100, 1995). A constitutively active mutant G-LP1 receptor can be constructed by substituting alternative amino acids at the corresponding residues in related receptors, e.g., substituting another amino acid for the homologue His in the glucagon-like peptide 1 (G-LP1) receptor. A similar change in any of the receptors related to PTH or G-LP1 by amino acid homology including, but not limited to, secretin, vasoactive intestinal polypeptide, glucagon, G-LP1, and calcitonin.

Non-peptide positive or inverse agonists identified in a screening assay employing any of the above-listed naturally occurring mutant receptors can be therapeutically useful against a corresponding adverse phenotype.

5. Strategies to identify synthetic mutant receptors.

Deletional analysis defines intracellular receptor domains important in second messenger signaling: Recombinant CCK-A and CCK-B/gastrin receptors are both coupled to phospholipase-C activation. Applicants hypothesized that the third intracellular loop of the CCK-B/gastrin receptor would include residues that are important in second messenger signaling. To test this hypothesis, a series of deletion mutations located in the third intracellular loop, each lacking between six and 55 amino acids, were expressed in COS-7 cells and tested for [$^{125}$I]CCK-8 binding and $^3$H inositol phosphate formation. Deletion of a twelve amino acid segment in the carboxy-terminal end of the third intracellular loop resulted in normal affinity for CCK-8s, but caused a 90% reduction of maximal inositol phosphate formation; all other receptors in this series signaled normally. The region containing the twelve amino acids that proved to functionally important was then screened for constitutively active point mutations, as described below.

Strategy 1: Domain swapping with cAMP generating receptors results in constitutive receptor activity: A method for rapidly identifying constitutively active mutant receptors relies on exchanging functional domains between two receptors, the domains being, e.g., approximately 5–10 amino acids in length. One of the two receptors is a form of the receptor which is the main template of the desired mutant receptor, e.g., a wild-type receptor; the second receptor is a different peptide hormone receptor from the first. Candidate receptors are coupled to different signal transduction pathways, e.g., a signal via a same or different second messenger pathways, yet are closely related in their amino acid sequence. These criteria are based on the idea that stretches of amino acids which function normally in their native context can confer agonist-independent signaling when transplanted into a closely related receptor which is linked to a different second-messenger signaling pathway.

The domain swapping strategy was used to identify constitutively active mutants of the CCK-B/gastrin receptor. A series of short segments in the third intracellular loop were sequentially replaced with homologous amino acid sequence from the vasopressin 2 receptor, which is the receptor most nearly identical in sequence to hCCK-B. Vasopressin 2 is also a good candidate for swapping domains with the CCK-B/gastrin receptor because it is, different from the latter, linked to the adenylate cyclase signaling pathway.

```
309           transmembrane domain VI   359
LT APGPGSGSRP TQAKLLAKKR VVRMLLVIVV LFFLCWLPVY SANTWR AFD  (SEQ ID NO: 8)
              AHVSA [MH40]                                 (SEQ ID NO: 9)
                 SA [MH128]                                (SEQ ID NO: 10)
                  S [MH156]                                (SEQ ID NO: 11)
                  E [MH162]                                (SEQ ID NO: 12)
```

Figure 9:
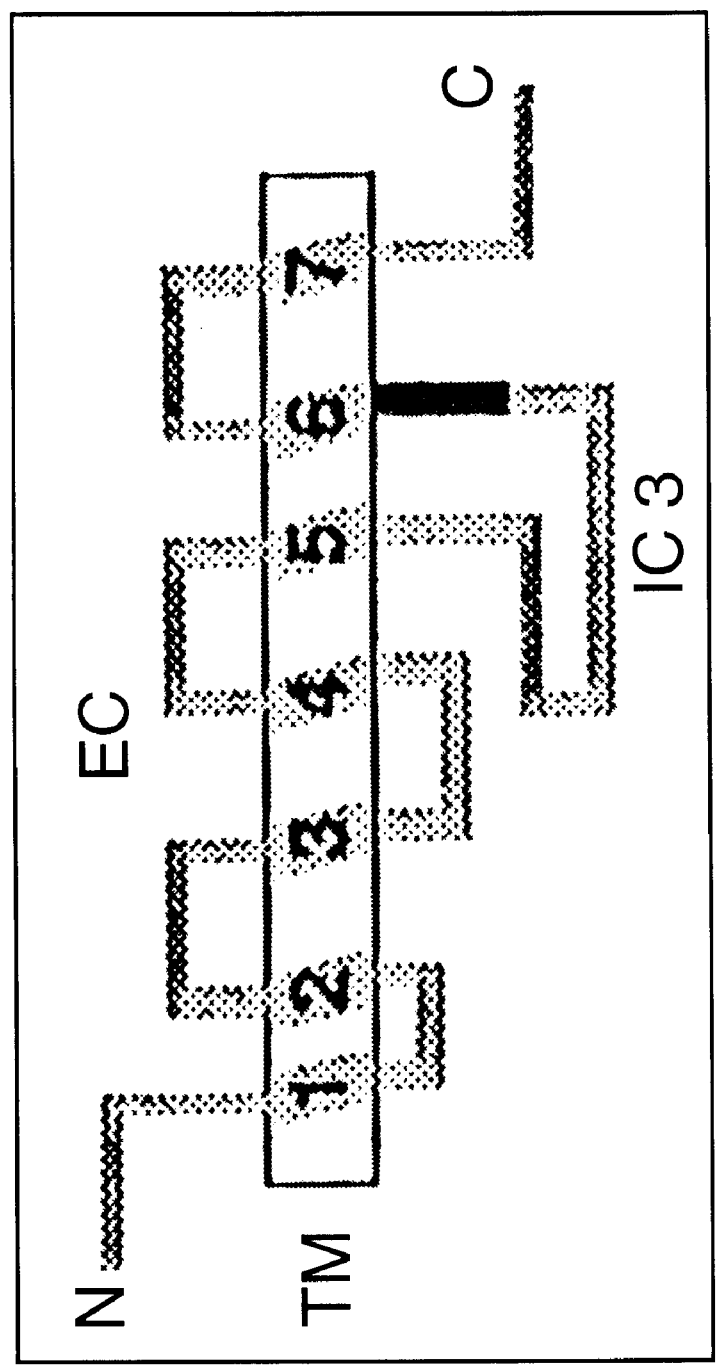
FIG. 9 is a schematic representation of the seven transmembrane (TM) domain structure of the human CCK-B/gastrin receptor. The C-terminal domain of the third intracellular loop is highlighted in black.

When tested, a five amino acid substitution (QAKLL (SEQ ID NO: 13 to AHVS (SEQ ID NO: 14) into the homologous position of the CCK-B/gastrin receptor resulted in constitutive activity of the CCK-B/gastrin receptor. The QAKLL (SEQ ID NO: 13) to AHVSA (SEQ ID NO: 14) substitution caused an increased level of basal inositol phosphate formation to 290% of the wild-type CCK-B/gastrin receptor (FIG. 9, Mutant 2). In addition, mutations causing constitutive activity include replacement of LL to SA, L to S, and L to E.

Strategy 2: Glutamic acid scanning mutagenesis identifies constitutively active receptors: In addition to, or as a substitute for, deletion analysis or domain swapping, mutant receptors can be made using a process Applicants have named 'amino acid scanning mutagenesis.' Amino acid scanning mutagenesis involves sequentially replacing each amino acid found in either an intracellular loop or in the half of the transmembrane domain flanking the intracellular portion of the receptor. An experimental option is to change the charge of the amino acid, e.g., to exchange a negative for a positive amino acid, a positive for a negative amino acid, or a positive or negative amino acid for a neutral amino acid. Another option would be to exchange each amino acid, e.g., each neutral amino acid, with another neutral amino acid.

In the case of the CCK-B/gastrin receptor, deletion analysis was initially used to define a functionally important twelve amino acid segment within the third intracellular loop which was important for second messenger signaling. Subsequently, each of the neutral amino acids within the 12 this segment was replaced sequentially with another amino acid, preferably with glutamic acid. The scanning analysis technique revealed that one of the glutamic acid substitutions caused a 228% increase in the basal-level of inositol phosphate accumulation, relative to the wild-type value, in transiently transfected COS-7 cells (FIG. 9, Mutant 1).

In this example, applicants focused on the region limited to the carboxy end of the third intracellular (IC) loop and the portion of the sixth transmembrane domain which flanks the third IC loop. Glutamic acid residues (E) were introduced in place of neutral amino acid residues.

```
309                    359
LT APGPGSGSRP TQAKLLAKKR VVRMLLVIVV LFFLCWLPVY SANTWR AFD
             |    ||    ||                              (SEQ ID NO:15)
             E E E EE                                   (SEQ ID NO:16)
```

Constitutively active receptors include an amino acid replacement of $^{323}$A→E (MH31, SEQ ID NO: 17), $^{324}$K→E (MH131, SEQ ID NO: 18), $^{325}$L→E (MH162, SEQ ID NO: 19), $^{327}$A→E (MH13, SEQ ID NO: 20) $^{331}$V→E (MH130, SEQ ID No: 21), $^{332}$V→E (129, SEQ ID NO: 22), and $^{331}$VV→EE (MH72), respectively all in pcDNAI vectors, as described above.

Figure 10:
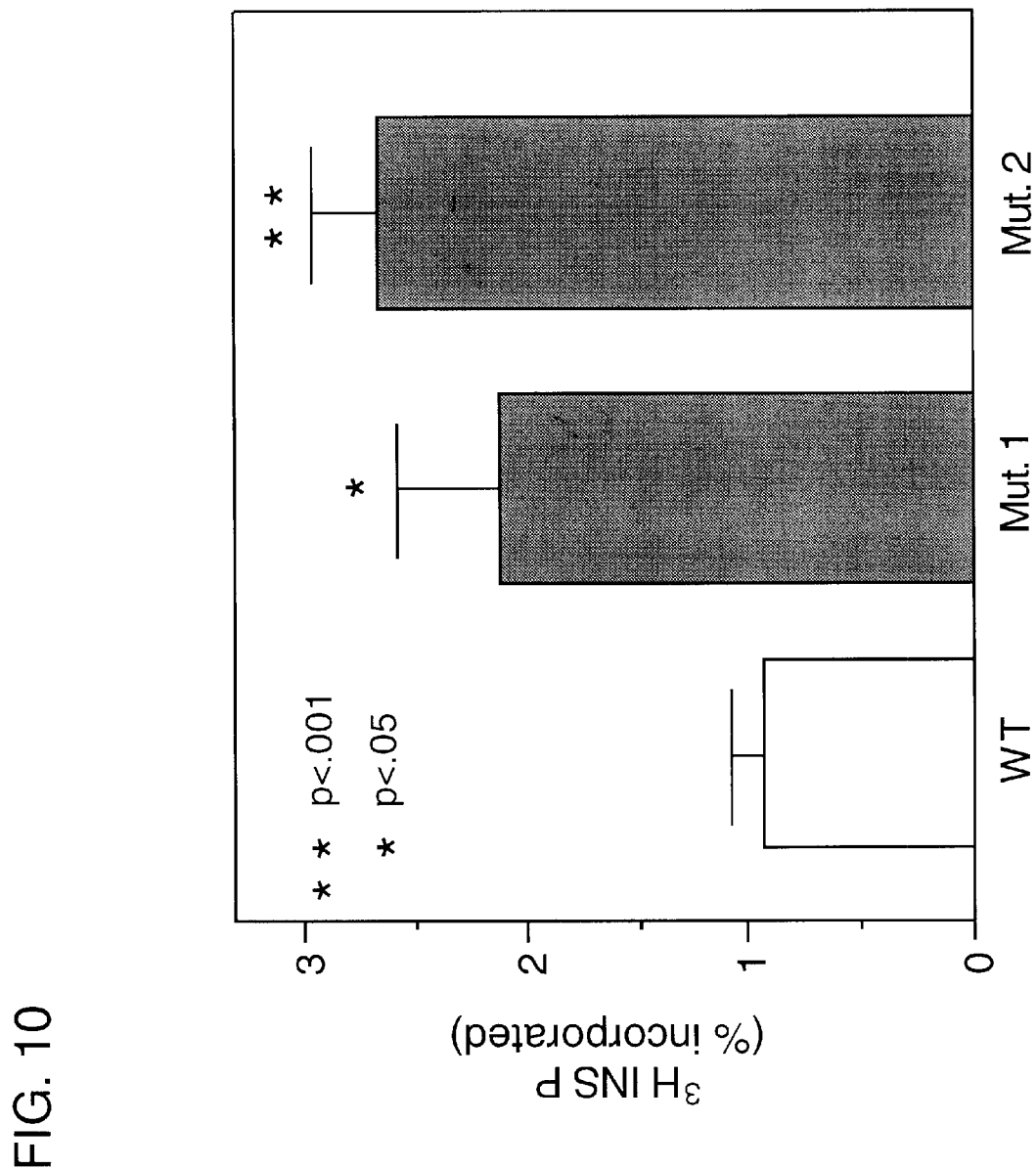
FIG. 10 is a bar graph of basal inositol phosphate accumulation in COS-7 cells transfected with wild-type CCK-B/gastrin receptor (WT), or with one of two constitutively active mutants (Mut.1, Mut.2).

FIG. 9 is a schematic representation of the seven transmembrane (TM) domain structure of the human CCK-B/gastrin receptor. The C-terminal domain of the third intracellular loop, which is crucial for intracellular signaling, is highlighted in black. Within this segment, two mutations were found to confer constitutive activity on the receptor. One of the mutations was constructed by glutamic acid substitution scanning (Mutant 1; MH129, SEQ ID NO: 22); a second mutation was constructed by domain swapping (Mutant 2; MH162, SEQ ID NO: 19). A bar graph showing the basal inositol phosphate accumulation in COS-7 cells, which had been transfected with the wild-type CCK-B/gastrin receptor or with two different constitutively active mutants, is shown in FIG. 10.

Strategy 3: A third method for making a mutant receptor is to align the receptor of interest with a known constitutively active mutant receptor, including, but not limited to, peptide hormone, biogenic amine, rhodopsin, or other G-protein coupled receptors. An example of such an alignment is shown in FIG. 2. Generally, mutations which result in constitutive activity in the known mutant can be introduced into the corresponding position of the receptor of interest. Examples of known constitutively active mutant receptors include, but are not limited to, the follicle stimulating hormone (FSH) receptor, the thyroid stimulating hormone (TSH) receptor, and the luteinizing hormone receptor, e.g., a 568 Ala to Val mutation in the LH receptor (Latronico et al., *J. Clin. Endo. & Meta.*, 80(8):2490–94, 1995).

This method, based on alignment, was employed to construct a CCK-A mutant receptor. A multiple alignment map was made which included the human and rat CCK-A sequences, the mastomys, rat, human, and canine CCK-B/gastrin receptor, and a Xenopus CCK-A/CCK-B intermediate receptor (CCK-XL; FIG. 2). Based on this map, conserved amino acids 138-ERY-140 of the CCK-A receptor were replaced with amino acids QRY, based on a known constitutively active rhodopsin mutant with enhanced transducin activation (Arnis et al., *J. Biol. Chem.*, 269:23879–81, 1994). The altered amino acid residues are positioned in transmembrane domain III and flank the second intracellular loop. Although the basal level of signaling was not increased, the intrinsic activity of the non-peptide ligand PD 135,158 was significantly increased.

Strategy 4: Additional mutant receptors can be made by sequentially deleting intracellular portions of the receptor, and looking for an increase in basal activity, or for overactivity of a partial agonist, relative to the wild-type receptor.

Wild-type Receptors with Enhanced Basal Activity:

Peptide hormone receptors useful in the method of the invention can include non-human receptors which have the ability to amplify the intrinsic activity of non-peptide agonist than does the corresponding human wild-type receptor, or which have a higher basal level of activity than does the human wild-type receptor.

Figure 11A:
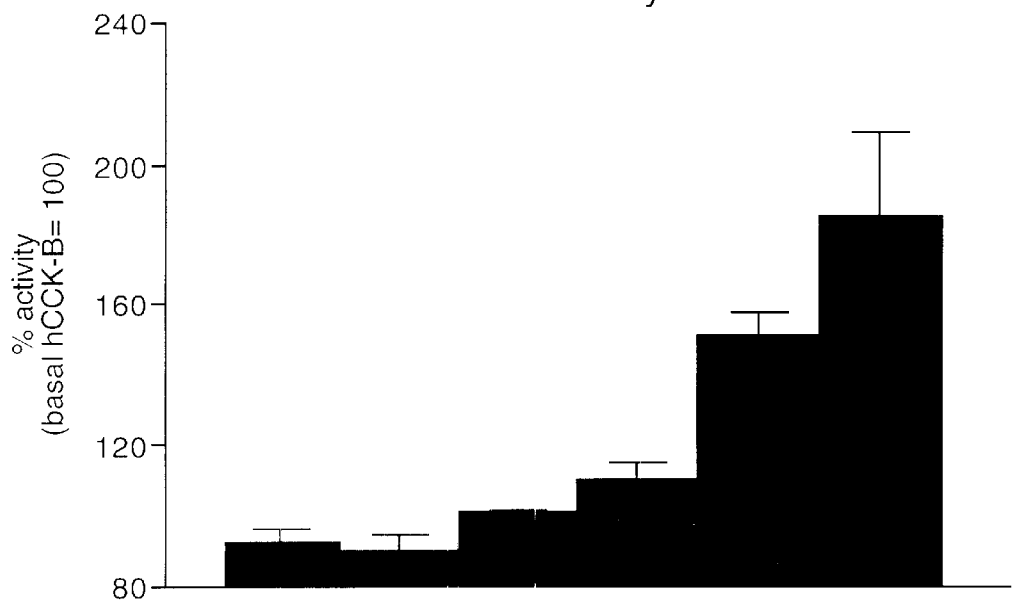
FIG. 11 is a bar graph showing a functional comparison of the CCK receptors human CCK-A (hCCK-A), human CCK-B (hCCK-B), dog CCK-B (dCCK-B), mouse CCK-B (mCCK-B), and the mastomys CCK receptor.
Figure 11B:
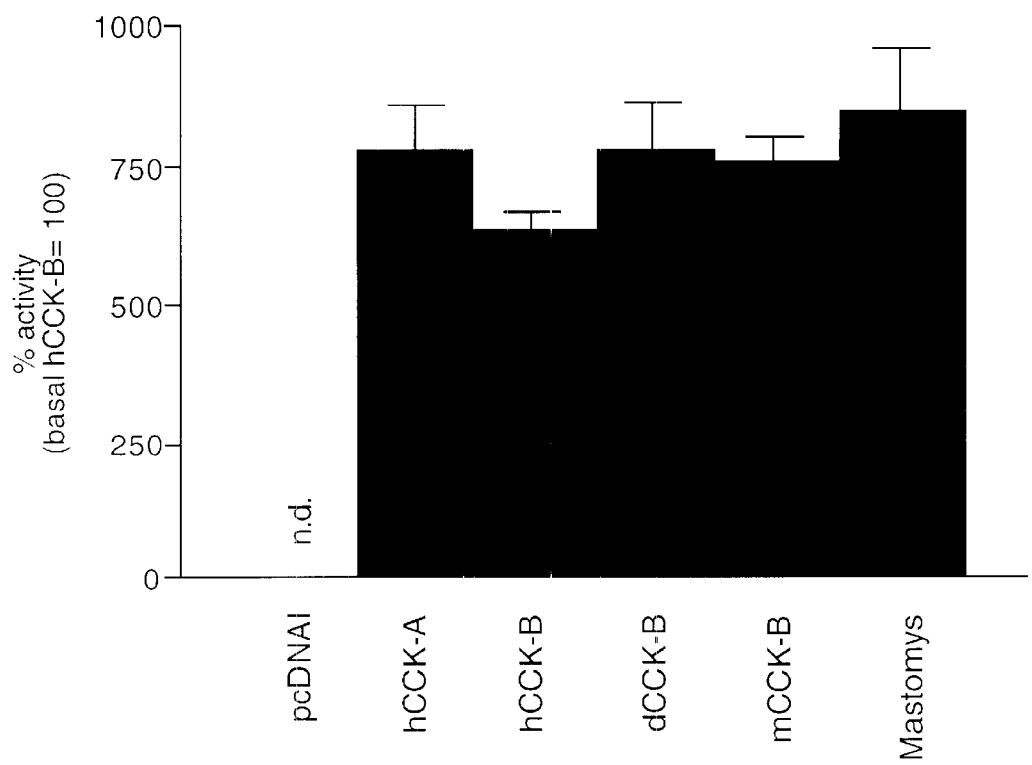

In FIG. 11, basal levels of inositol phosphate production were measured for human CCK-A hCCK-A), human CCK-B (hCCK-B), dog CCK-B (dCCK-B), mouse CCK-B (mCCK-B), and the mastomys CCK receptor (FIG. 11, part A), and expressed relative to the basal level of hCCK-B.

Single experiments were also performed for the rat CCK-B/gastrin receptor and for the related Xenopus CCK receptor (Table 2). The human $^{325}$L to E mutant served as a positive control (n=−14).

TABLE 2

| receptor | basal (% of human basal) | CCK-8s stimulated (% human basal) |
|---|---|---|
| rat CCK-A | 77 | 684 |
| Xenopus CCK | 74 | 442 |
| $^{325}$L to E CCKA | 231 ± 7 | 771 ± 36 |

The wild-type human CCK-A and CCK-B/gastrin receptors induced only insignificant changes of basal inositol phosphate production in COS-7 cells (as compared to control cells transfected with the empty plasmid vector, pCDNAI). Similarly, the wild-type rat CCK-A and canine CCK-B/gastrin receptors, as well as the closely related Xenopus CCK receptor all appeared more or less functionally silent in the basal state. In contrast, the wild type mouse CCK-B/gastrin receptor and its homologue from mastomys natalensis significantly increased basal inositol phosphate production in COS-7 cells over pcDNAI controls. When compared with the slight basal activity of the wild type human CCK-B/gastrin receptor, it was estimated that the basal activities of the wild type mouse and mastomys homologues were 7- and 11-fold higher, respectively. For comparison, the $^{325}$L→E mutant of the human CCK-B/gastrin receptor appeared to be at least 16-fold more active than the human wild type receptor in its basal state. It should be noted that the described species differences in basal activities were clearly not related to different degrees of receptor expression, since the maximal response to stimulation with CCK-8s was comparable for all tested receptors (positive control).

IV. Therapeutic Use.

The ability to pharmacologically modulate wild-type or constitutively active receptor activity opens the door for a new class of clinically useful drugs. Enhanced receptors will enable the discovery of novel drugs directed at a broad spectrum of diseases. Constitutively active mutants of the thyrotropin, luteinizing hormone, and parathyroid hormone receptors are already known to occur in nature (see above) and might provide a starting point for non-peptide agonist/inverse agonist screening. For example, drugs which silence constitutively active thyroid stimulating hormone receptors, which are implicated in the etiology of thyroid adenomas, could be used to inhibit tumor growth. Similarly, in patients with constitutively active luteinizing hormone receptors, inverse agonists could delay the onset of precocious puberty.

Further information on peptide hormone receptor amino acid sequences, receptor-specific agonists and antagonists, receptor conformation, pharmacology, receptor-encoding genes, animal models for subsequent follow-up studies, and database accession numbers can be obtained from: Watson and Arkinstall, *The G-Protein Linked Receptor*, Academic Press, NY., 1994; see also, Kolakowski, L. F., "The G Protein-Coupled Receptor Database", World-Wide-Web Site, GCRDB-WWW.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions.

Other embodiments are within the following claims.

What is claimed is:

1. A screening method comprising:
    (a) providing an enhanced chimeric G protein-coupled peptide hormone receptor that signals through the same pathway as a respective wild-type G protein-coupled receptor, in which a region of a functional domain of a first peptide hormone receptor is replaced with a corresponding region of a functional domain of a second peptide hormone receptor, wherein said functional domain is selected from the group consisting of an intracellular loop and a transmembrane domain; wherein the ability of said chimeric peptide hormone receptor to amplify an agonist signal is greater than the ability of the first peptide hormone receptor to amplify said agonist signal; and
    (b) using said chimeric peptide hormone receptor to screen ligands for agonist activity.

2. The method of claim 1, wherein the first peptide hormone receptor is a CCK-B/gastrin receptor.

3. The method of claim 1, wherein the second peptide hormone receptor is a vasopressin 2 receptor.

4. The method of claim 1, wherein the chimeric receptor has, in place of a functional domain of a CCK-B/gastrin receptor, a functional domain of a vasopressin 2 receptor.

5. The method of claim 4, wherein said functional domain of said CCK-B/gastrin receptor comprises the third intracellular loop and the amino acid sequence QAKLL (SEQ ID NO: 13) found in said third intracellular loop is replaced with the amino acid sequence AHVSA (SEQ ID NO: 9).

6. The method of claim 4, wherein said functional domain of said CCK-B/gastrin receptor comprises the amino acid sequence found at positions 322 to 326 of the human CCK-B/gastrin receptor (SEQ ID NO: 3) and said amino acid sequence is replaced with the amino acid sequence AHVSA (SEQ ID NO: 9).

7. The method of claim 4, wherein said functional domain of said CCK-B/gastrin receptor comprises the amino acid found at position 325 to 326 of the human CCK-B/gastrin receptor (SEQ ID NO: 3) and said amino acid is replaced with an amino acid sequence SA.

8. The method of claim 4, wherein said functional domain of said CCK-B/gastrin receptor comprises the amino acid found at position 325 of the human CCK-B/gastrin receptor (SEQ ID NO: 3) and said amino acid is replaced with an amino acid selected from the group consisting of S and E.

* * * * *

UNITED STATES PATENT AND TRADEMARK OFFICE
CERTIFICATE OF CORRECTION

PATENT NO. : 6,376,198 B1  Page 1 of 1
DATED : April 23, 2002
INVENTOR(S) : Alan S. Kopin et al.

It is certified that error appears in the above-identified patent and that said Letters Patent is hereby corrected as shown below:

Title page,
Item [56], References Cited, PUBLICATIONS, replace "Techykinin" with -- Tachykinin --;

Column 10,
Line 17, replace "CCKB" with -- CCK-B --;

Column 11,
Line 4, replace "ca2$^+$" with -- Ca$^{2+}$ --;
Line 23, replace "P3" with -- P$_3$ --;

Column 14,
Line 37, replace "AHVS" with -- AHVSA --;

Column 16,
Line 21, replace "hCCK-A)" with -- (hCCK-A) --; and

Column 46,
Lines 4 and 6, after "acid" insert -- sequence --.

Signed and Sealed this

Seventh Day of October, 2003

JAMES E. ROGAN
*Director of the United States Patent and Trademark Office*

```
                          SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 449 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

Met Glu Leu Leu Lys Leu Asn Ser Ser Val Gln Gly Pro Gly Pro Gly
1               5                   10                  15

Ser Gly Ser Ser Leu Cys His Pro Gly Val Ser Leu Leu Asn Ser Ser
                20                  25                  30

Ala Gly Asn Leu Ser Cys Glu Pro Pro Arg Ile Arg Gly Thr Gly Thr
            35                  40                  45

Arg Glu Leu Glu Leu Ala Ile Arg Ile Thr Leu Tyr Ala Val Ile Phe
    50                  55                  60

Leu Met Ser Ile Gly Gly Asn Met Leu Ile Ile Val Val Leu Gly Leu
65                  70                  75                  80

Ser Arg Arg Leu Arg Thr Val Thr Asn Ala Phe Leu Leu Ser Leu Ala
                85                  90                  95

Val Ser Asp Leu Leu Leu Ala Val Ala Cys Met Pro Phe Thr Leu Leu
            100                 105                 110

Pro Asn Leu Met Gly Thr Phe Ile Phe Gly Thr Val Ile Cys Lys Ala
        115                 120                 125

Val Ser Tyr Leu Met Gly Val Ser Val Ser Val Ser Thr Leu Asn Leu
    130                 135                 140

Val Ala Ile Ala Leu Glu Arg Tyr Ser Ala Ile Cys Arg Pro Leu Gln
145                 150                 155                 160

Ala Arg Val Trp Gln Thr Arg Ser His Ala Ala Arg Val Ile Leu Ala
                165                 170                 175

Thr Trp Leu Leu Ser Gly Leu Leu Met Val Pro Tyr Pro Val Tyr Thr
            180                 185                 190

Val Val Gln Pro Val Gly Pro Arg Val Leu Gln Cys Met His Arg Trp
        195                 200                 205

Pro Ser Ala Arg Val Arg Gln Thr Trp Ser Val Leu Leu Leu Met Leu
    210                 215                 220
```

```
Leu Phe Phe Ile Pro Gly Val Met Ala Val Ala Tyr Gly Leu Ile
225                 230                 235                 240

Ser Arg Glu Leu Tyr Leu Gly Leu Arg Phe Asp Gly Asp Asn Asp Ser
            245                 250                 255

Asp Thr Gln Ser Arg Val Arg Asn Gln Gly Gly Leu Pro Gly Gly Thr
            260                 265                 270

Ala Pro Gly Pro Val His Gln Asn Gly Gly Cys Arg His Val Thr Val
            275                 280                 285

Ala Gly Glu Asp Asn Asp Gly Cys Tyr Val Gln Leu Pro Arg Ser Arg
            290                 295                 300

Leu Glu Met Thr Thr Leu Thr Thr Pro Thr Pro Gly Pro Gly Leu Ala
305                 310                 315                 320

Ser Ala Asn Gln Ala Lys Leu Leu Ala Lys Lys Arg Val Val Arg Met
                325                 330                 335

Leu Leu Val Ile Val Leu Leu Phe Phe Leu Cys Trp Leu Pro Ile Tyr
                340                 345                 350

Ser Ala Asn Thr Trp Cys Ala Phe Asp Gly Pro Gly Ala Met Arg Ala
                355                 360                 365

Leu Ser Gly Ala Pro Ile Ser Phe Ile His Leu Leu Ser Tyr Ala Ser
370                 375                 380

Ala Cys Val Asn Pro Leu Val Tyr Cys Phe Met His Arg Arg Phe Arg
385                 390                 395                 400

Gln Ala Cys Leu Asp Thr Cys Ala Arg Cys Cys Pro Arg Pro Pro Arg
                405                 410                 415

Ala Arg Pro Arg Pro Leu Pro Asp Glu Asp Pro Pro Thr Pro Ser Ile
                420                 425                 430

Ala Ser Leu Ser Arg Leu Ser Tyr Thr Thr Ile Ser Thr Leu Gly Pro
                435                 440                 445

Gly (2) INFORMATION FOR SEQ ID NO:2:

(i) SEQUENCE CHARACTERISTICS:
        (A) LENGTH: 451 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

Met Glu Leu Leu Lys Leu Asn Arg Ser Val Gln Gly Pro Gly Pro Gly
1               5                   10                  15

Ser Gly Ser Ser Leu Cys Arg Pro Gly Val Ser Leu Leu Asn Ser Ser
                20                  25                  30

Ser Ala Gly Asn Leu Ser Cys Asp Pro Pro Arg Ile Arg Gly Thr Gly
            35                  40                  45

Thr Arg Glu Leu Glu Met Ala Ile Arg Ile Thr Leu Tyr Ala Val Ile
50                  55                  60

Phe Leu Met Ser Val Gly Gly Asn Val Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
```

-continued

```
            115                 120                 125
Ala Ile Ser Tyr Leu Met Gly Val Ser Val Ser Thr Leu Asn
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Leu
                165                 170                 175

Ala Thr Trp Leu Leu Ser Gly Leu Leu Met Val Pro Tyr Pro Val Tyr
            180                 185                 190

Thr Met Val Gln Pro Val Gly Pro Arg Val Leu Gln Cys Met His Arg
        195                 200                 205

Trp Pro Ser Ala Arg Val Gln Gln Thr Trp Ser Val Leu Leu Leu Leu
210                 215                 220

Leu Leu Phe Phe Ile Pro Gly Val Val Ile Ala Val Ala Tyr Gly Leu
225                 230                 235                 240

Ile Ser Arg Glu Leu Tyr Leu Gly Leu His Phe Asp Gly Glu Asn Asp
                245                 250                 255

Ser Glu Thr Gln Ser Arg Ala Arg Asn Gln Gly Gly Leu Pro Gly Gly
            260                 265                 270

Ala Ala Pro Gly Pro Val His Gln Asn Gly Gly Cys Arg Pro Val Thr
            275                 280                 285

Ser Val Ala Gly Glu Asp Ser Asp Gly Cys Cys Val Gln Leu Pro Arg
290                 295                 300

Ser Arg Leu Glu Met Thr Thr Leu Thr Thr Pro Thr Gly Pro Val Pro
305                 310                 315                 320

Gly Pro Arg Pro Asn Gln Ala Lys Leu Leu Ala Lys Lys Arg Val Val
                325                 330                 335

Arg Met Leu Leu Val Ile Val Leu Leu Phe Phe Leu Cys Trp Leu Pro
            340                 345                 350

Val Tyr Ser Val Asn Thr Trp Arg Ala Phe Asp Gly Pro Gly Ala Gln
            355                 360                 365

Arg Ala Leu Ser Gly Ala Pro Ile Ser Phe Ile His Leu Leu Ser Tyr
    370                 375                 380

Val Ser Ala Cys Val Asn Pro Leu Val Tyr Cys Phe Met His Arg Arg
385                 390                 395                 400

Phe Arg Gln Ala Cys Leu Asp Thr Cys Ala Arg Cys Cys Pro Arg Pro
                405                 410                 415

Pro Arg Ala Arg Pro Gln Pro Leu Pro Asp Glu Asp Pro Pro Thr Pro
                420                 425                 430

Ser Ile Ala Ser Leu Ser Arg Leu Ser Tyr Thr Thr Ile Ser Thr Leu
            435                 440                 445

Gly Pro Gly
    450
```

(2) INFORMATION FOR SEQ ID NO:3:

(i) SEQUENCE CHARACTERISTICS:
        (A) LENGTH: 448 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Met Glu Leu Leu Lys Leu Asn Arg Ser Val Gln Gly Thr Gly Pro Gly

-continued

```
1               5                   10                  15

Pro Gly Ala Ser Leu Cys Arg Pro Gly Ala Pro Leu Leu Asn Ser Ser
                20                  25              30

Ser Val Gly Asn Leu Ser Cys Glu Pro Pro Arg Ile Arg Gly Ala Gly
            35                  40              45

Thr Arg Glu Leu Glu Leu Ala Ile Arg Ile Thr Leu Tyr Ala Val Ile
        50                  55              60

Phe Leu Met Ser Val Gly Gly Asn Met Leu Ile Ile Val Val Leu Gly
65                  70              75                      80

Leu Ser Arg Arg Leu Arg Thr Val Thr Asn Ala Phe Leu Leu Ser Leu
                85                  90              95

Ala Val Ser Asp Leu Leu Leu Ala Val Ala Cys Met Pro Phe Thr Leu
            100                 105             110

Leu Pro Asn Leu Met Gly Thr Phe Ile Phe Gly Thr Val Ile Cys Lys
            115                 120             125

Ala Val Ser Tyr Leu Met Gly Val Ser Val Ser Val Ser Thr Leu Ser
            130                 135             140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170             175

Ala Thr Trp Leu Leu Ser Gly Leu Leu Met Val Pro Tyr Pro Val Tyr
                180                 185             190

Thr Val Val Gln Pro Val Gly Pro Arg Val Leu Gln Cys Val His Arg
            195                 200             205

Trp Pro Ser Ala Arg Val Arg Gln Thr Trp Ser Val Leu Leu Leu Leu
        210                 215             220

Leu Leu Phe Phe Ile Pro Gly Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250             255

Ser Asp Ser Gln Ser Arg Val Arg Asn Gln Gly Gly Leu Pro Gly Ala
            260                 265             270

Val His Gln Asn Gly Arg Cys Arg Pro Glu Thr Gly Ala Val Gly Glu
            275                 280             285

Asp Ser Asp Gly Cys Tyr Val Gln Leu Pro Arg Ser Arg Pro Ala Leu
            290                 295             300

Glu Leu Thr Ala Leu Thr Ala Pro Gly Pro Gly Ser Gly Ser Arg
305                 310                 315                 320

Pro Thr Gln Ala Lys Leu Leu Ala Lys Lys Arg Val Val Arg Met Leu
                325                 330             335

Leu Val Ile Val Val Leu Phe Phe Leu Cys Trp Leu Pro Val Tyr Ser
            340                 345             350

Ala Asn Thr Trp Arg Ala Phe Asp Gly Pro Gly Ala His Arg Ala Leu
            355                 360             365

Ser Gly Ala Pro Ile Ser Phe Ile His Leu Leu Ser Tyr Ala Ser Ala
            370                 375             380

Cys Val Asn Pro Leu Val Tyr Cys Phe Met His Arg Arg Phe Arg Gln
385                 390                 395                 400

Ala Cys Leu Glu Thr Cys Ala Arg Cys Cys Pro Arg Pro Pro Arg Ala
            405                 410             415

Arg Pro Arg Ala Leu Pro Asp Glu Asp Pro Pro Thr Pro Ser Ile Ala
            420                 425             430
```

```
Ser Leu Ser Arg Leu Ser Tyr Thr Thr Ile Ser Thr Leu Gly Pro Gly
        435                 440                 445

(2) INFORMATION FOR SEQ ID NO:4:

(i) SEQUENCE CHARACTERISTICS:
        (A) LENGTH: 453 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

Met Glu Leu Leu Lys Leu Asn Arg Ser Ala Gln Gly Ser Gly Ala Gly
1               5                   10                  15

Pro Gly Ala Ser Leu Cys Arg Ala Gly Gly Ala Leu Leu Asn Ser Ser
            20                  25                  30

Gly Ala Gly Asn Leu Ser Cys Glu Pro Pro Arg Leu Arg Gly Ala Gly
        35                  40                  45

Thr Arg Glu Leu Glu Leu Ala Ile Arg Val Thr Leu Tyr Ala Val Ile
    50                  55                  60

Phe Leu Met Ser Val Gly Gly Asn Val Leu Ile Ile Val Val Leu Gly
65              70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Val Cys Lys
        115                 120                 125

Ala Val Ser Tyr Leu Met Gly Val Ser Val Ser Val Ser Thr Leu Ser
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Ile
                165                 170                 175

Ala Thr Trp Met Leu Ser Gly Leu Leu Met Val Pro Tyr Pro Val Tyr
            180                 185                 190

Thr Ala Val Gln Pro Ala Gly Gly Ala Arg Ala Leu Gln Cys Val His
        195                 200                 205

Arg Trp Pro Ser Ala Arg Val Arg Gln Thr Trp Ser Val Leu Leu Leu
    210                 215                 220

Leu Leu Leu Phe Phe Val Pro Gly Val Val Met Ala Val Ala Tyr Gly
225                 230                 235                 240

Leu Ile Ser Arg Glu Leu Tyr Leu Gly Leu Arg Phe Asp Glu Asp Ser
                245                 250                 255

Asp Ser Glu Ser Arg Val Arg Ser Gln Gly Gly Leu Arg Gly Gly Ala
            260                 265                 270

Gly Pro Gly Pro Ala Pro Pro Asn Gly Ser Cys Arg Pro Glu Gly Gly
        275                 280                 285

Leu Ala Gly Glu Asp Gly Asp Gly Cys Tyr Val Gln Leu Pro Arg Ser
    290                 295                 300

Arg Gln Thr Leu Glu Leu Ser Ala Leu Thr Ala Pro Thr Pro Gly Pro
305                 310                 315                 320

Gly Gly Gly Pro Arg Pro Tyr Gln Ala Lys Leu Leu Ala Lys Lys Arg
                325                 330                 335
```

```
Val Val Arg Met Leu Leu Val Ile Val Val Leu Phe Phe Leu Cys Trp
                340                 345                 350
Leu Pro Leu Tyr Ser Ala Asn Thr Trp Arg Ala Phe Asp Ser Ser Gly
        355                 360                 365
Ala His Arg Ala Leu Ser Gly Ala Pro Ile Ser Phe Ile His Leu Leu
        370                 375                 380
Ser Tyr Ala Ser Ala Cys Val Asn Pro Leu Val Tyr Cys Phe Met His
385                 390                 395                 400
Arg Arg Phe Arg Gln Ala Cys Leu Glu Thr Cys Ala Arg Cys Cys Pro
                405                 410                 415
Arg Pro Pro Arg Ala Arg Pro Arg Pro Leu Pro Asp Glu Asp Pro Pro
                420                 425                 430
Thr Pro Ser Ile Ala Ser Leu Ser Arg Leu Ser Tyr Thr Thr Ile Ser
        435                 440                 445
Thr Leu Gly Pro Gly
    450
```

(2) INFORMATION FOR SEQ ID NO:5:

(i) SEQUENCE CHARACTERISTICS:
        (A) LENGTH: 428 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
Met Asp Val Val Asp Ser Leu Leu Val Asn Gly Ser Asn Ile Thr Pro
1                   5                   10                  15
Pro Cys Glu Leu Gly Leu Glu Asn Glu Thr Leu Phe Cys Leu Asp Gln
                20                  25                  30
Pro Arg Pro Ser Lys Glu Trp Gln Pro Ala Val Gln Ile Leu Leu Tyr
            35                  40                  45
Ser Leu Ile Phe Leu Leu Ser Val Leu Gly Asn Thr Leu Val Ile Thr
        50                  55                  60
Val Leu Ile Arg Asn Lys Arg Met Arg Thr Val Thr Asn Ile Phe Leu
65                  70                  75                  80
Leu Ser Leu Ala Val Ser Asp Leu Met Leu Cys Leu Phe Cys Met Pro
                85                  90                  95
Phe Asn Leu Ile Pro Asn Leu Leu Lys Asp Phe Ile Phe Gly Ser Ala
                100                 105                 110
Val Cys Lys Thr Thr Thr Tyr Phe Met Gly Thr Ser Val Ser Val Ser
            115                 120                 125
Thr Phe Asn Leu Val Ala Ile Ser Leu Glu Arg Tyr Gly Ala Ile Cys
        130                 135                 140
Lys Pro Leu Gln Ser Arg Val Trp Gln Thr Lys Ser His Ala Leu Lys
145                 150                 155                 160
Val Ile Ala Ala Thr Trp Cys Leu Ser Phe Thr Ile Met Thr Pro Tyr
                165                 170                 175
Pro Ile Tyr Ser Asn Leu Val Pro Phe Thr Lys Asn Asn Asn Gln Thr
                180                 185                 190
Ala Asn Met Cys Arg Phe Leu Leu Pro Asn Asp Val Met Gln Gln Ser
            195                 200                 205
Trp His Thr Phe Leu Leu Leu Ile Leu Phe Leu Ile Pro Gly Ile Val
        210                 215                 220
```

-continued

Met Met Val Ala Tyr Gly Leu Ile Ser Leu Glu Leu Tyr Gln Gly Ile
225                 230                 235                 240

Lys Phe Glu Ala Ser Gln Lys Lys Ser Ala Lys Glu Arg Lys Pro Ser
            245                 250                 255

Thr Thr Ser Ser Gly Lys Tyr Glu Asp Ser Asp Gly Cys Tyr Leu Gln
            260                 265                 270

Lys Thr Arg Pro Pro Arg Lys Leu Glu Leu Arg Gln Leu Ser Thr Gly
            275                 280                 285

Ser Ser Ser Arg Ala Asn Arg Ile Arg Ser Asn Ser Ser Ala Ala Asn
    290                 295                 300

Leu Met Ala Lys Lys Arg Val Ile Arg Met Leu Ile Val Ile Val Val
305                 310                 315                 320

Leu Phe Phe Leu Cys Trp Met Pro Ile Phe Ser Ala Asn Ala Trp Arg
                325                 330                 335

Ala Tyr Asp Thr Ala Ser Ala Glu Arg Arg Leu Ser Gly Thr Pro Ile
            340                 345                 350

Ser Phe Ile Leu Leu Leu Ser Tyr Thr Ser Ser Cys Val Asn Pro Ile
            355                 360                 365

Ile Tyr Cys Phe Met Asn Lys Arg Phe Arg Leu Gly Phe Met Ala Thr
    370                 375                 380

Phe Pro Cys Cys Pro Asn Pro Gly Pro Pro Gly Ala Arg Gly Glu Val
385                 390                 395                 400

Gly Glu Glu Glu Glu Gly Gly Thr Thr Gly Ala Ser Leu Ser Arg Phe
                405                 410                 415

Ser Tyr Ser His Met Ser Ala Ser Val Pro Pro Gln
            420                 425

(2) INFORMATION FOR SEQ ID NO:6:

(i) SEQUENCE CHARACTERISTICS:
        (A) LENGTH: 443 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Met Ser His Ser Pro Ala Arg Gln His Leu Val Glu Ser Ser Arg Met
1               5                   10                  15

Asp Val Val Asp Ser Leu Leu Met Asn Gly Ser Asn Ile Thr Pro Pro
            20                  25                  30

Cys Glu Leu Gly Leu Glu Asn Glu Thr Leu Phe Cys Leu Asp Gln Pro
            35                  40                  45

Gln Pro Ser Lys Glu Trp Gln Ser Ala Leu Gln Ile Leu Leu Tyr Ser
    50                  55                  60

Ile Ile Phe Leu Leu Ser Val Leu Gly Asn Thr Leu Val Ile Thr Val
65                  70                  75                  80

Leu Ile Arg Asn Lys Arg Met Arg Thr Val Thr Asn Ile Phe Leu Leu
            85                  90                  95

Ser Leu Ala Val Ser Asp Leu Met Leu Cys Phe Cys Met Pro Phe Asn
            100                 105                 110

Leu Ile Pro Asn Leu Leu Lys Asp Phe Ile Phe Gly Ser Ala Val Cys
            115                 120                 125

Lys Thr Thr Thr Tyr Phe Met Gly Thr Ser Val Ser Val Ser Thr Phe
            130                 135                 140

```
Asn Leu Val Ala Ile Ser Leu Glu Arg Tyr Gly Ala Ile Cys Arg Pro
145                 150                 155                 160

Leu Gln Ser Arg Val Trp Gln Thr Lys Ser His Ala Leu Lys Val Ile
                165                 170                 175

Ala Ala Thr Trp Cys Leu Ser Phe Thr Ile Met Thr Pro Tyr Pro Ile
            180                 185                 190

Tyr Ser Asn Leu Val Pro Phe Thr Lys Asn Asn Asn Gln Thr Ala Asn
        195                 200                 205

Met Cys Arg Phe Leu Leu Pro Ser Asp Ala Met Gln Gln Ser Trp Gln
210                 215                 220

Thr Phe Leu Leu Leu Ile Leu Phe Leu Leu Pro Gly Ile Val Met Val
225                 230                 235                 240

Val Ala Tyr Gly Leu Ile Ser Leu Glu Leu Tyr Gln Gly Ile Lys Phe
                245                 250                 255

Asp Ala Ser Gln Lys Lys Ser Ala Lys Glu Lys Lys Pro Ser Thr Gly
            260                 265                 270

Ser Ser Thr Arg Tyr Glu Asp Ser Asp Gly Cys Tyr Leu Gln Lys Ser
        275                 280                 285

Arg Pro Pro Arg Lys Leu Glu Leu Gln Gln Leu Ser Ser Gly Ser Gly
290                 295                 300

Gly Ser Arg Leu Asn Arg Ile Arg Ser Ser Ser Ala Ala Asn Leu
305                 310                 315                 320

Ile Ala Lys Lys Arg Val Ile Arg Met Leu Ile Val Ile Val Val Leu
                325                 330                 335

Phe Phe Leu Cys Trp Met Pro Ile Phe Ser Ala Asn Ala Trp Arg Ala
            340                 345                 350

Tyr Asp Thr Val Ser Ala Glu Lys His Leu Ser Gly Thr Pro Ile Ser
        355                 360                 365

Phe Ile Leu Leu Leu Ser Tyr Thr Ser Ser Cys Val Asn Pro Ile Ile
        370                 375                 380

Tyr Cys Phe Met Asn Lys Arg Phe Arg Leu Gly Phe Met Ala Thr Phe
385                 390                 395                 400

Pro Cys Cys Pro Asn Pro Gly Pro Pro Gly Val Arg Gly Glu Val Gly
                405                 410                 415

Glu Glu Glu Asp Gly Arg Thr Ile Arg Ala Leu Leu Ser Arg Tyr Ser
            420                 425                 430

Tyr Ser His Met Ser Thr Ser Ala Pro Pro
            435                 440

(2) INFORMATION FOR SEQ ID NO:7:

(i) SEQUENCE CHARACTERISTICS:
        (A) LENGTH: 453 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

Met Glu Ser Leu Arg Ser Leu Ser Asn Ile Ser Ala Leu His Glu Leu
1               5                   10                  15

Leu Cys Arg Tyr Ser Asn Leu Ser Gly Thr Leu Thr Trp Asn Leu Ser
            20                  25                  30

Ser Thr Asn Gly Thr His Asn Leu Thr Thr Ala Asn Trp Pro Pro Trp
        35                  40                  45
```

```
Asn Leu Asn Cys Thr Pro Ile Leu Asp Arg Lys Lys Pro Ser Pro Ser
    50                  55                  60

Asp Leu Asn Leu Trp Val Arg Ile Val Met Tyr Ser Val Ile Phe Leu
65                  70                  75                  80

Leu Ser Val Phe Gly Asn Thr Leu Ile Ile Val Leu Val Met Asn
                85                  90                  95

Lys Arg Leu Arg Thr Ile Thr Asn Ser Phe Leu Leu Ser Leu Ala Leu
                100                 105                 110

Ser Asp Leu Met Val Ala Val Leu Cys Met Pro Phe Thr Leu Ile Pro
            115                 120                 125

Asn Leu Met Glu Asn Phe Ile Phe Gly Glu Val Ile Cys Arg Ala Ala
        130                 135                 140

Ala Tyr Phe Met Gly Leu Ser Val Ser Val Ser Thr Phe Asn Leu Val
145                 150                 155                 160

Ala Ile Ser Ile Glu Arg Tyr Ser Ala Ile Cys Asn Pro Leu Xaa Ser
                165                 170                 175

Arg Val Trp Gln Thr Arg Ser His Ala Tyr Arg Val Ile Ala Ala Thr
                180                 185                 190

Trp Val Leu Ser Ser Ile Ile Met Ile Pro Tyr Leu Val Tyr Asn Lys
            195                 200                 205

Thr Val Thr Phe Pro Met Lys Asp Arg Arg Val Gly His Gln Cys Arg
        210                 215                 220

Leu Val Trp Pro Ser Lys Gln Val Gln Gln Ala Trp Tyr Val Leu Leu
225                 230                 235                 240

Leu Thr Ile Leu Phe Phe Ile Pro Gly Val Val Met Ile Val Ala Tyr
                245                 250                 255

Gly Leu Ile Ser Arg Glu Leu Tyr Arg Gly Ile Gln Phe Glu Met Asp
                260                 265                 270

Leu Asn Lys Glu Ala Lys Ala His Lys Asn Gly Val Ser Thr Pro Thr
            275                 280                 285

Thr Ile Pro Ser Gly Asp Glu Gly Asp Gly Cys Tyr Ile Gln Val Thr
        290                 295                 300

Lys Arg Arg Asn Thr Met Glu Met Ser Thr Leu Thr Pro Ser Val Cys
305                 310                 315                 320

Thr Lys Met Asp Arg Ala Arg Ile Asn Asn Ser Glu Ala Lys Leu Met
                325                 330                 335

Ala Lys Lys Arg Val Ile Arg Met Leu Ile Val Ile Val Ala Met Phe
                340                 345                 350

Phe Ile Cys Trp Met Pro Ile Phe Val Ala Asn Thr Trp Lys Ala Phe
            355                 360                 365

Asp Glu Leu Ser Ala Phe Asn Thr Leu Thr Gly Ala Pro Ile Ser Phe
        370                 375                 380

Ile His Leu Leu Ser Tyr Thr Ser Ala Cys Val Asn Pro Leu Ile Tyr
385                 390                 395                 400

Cys Phe Met Asn Lys Arg Phe Arg Lys Ala Phe Leu Gly Thr Phe Ser
                405                 410                 415

Ser Cys Ile Lys Pro Cys Arg Asn Phe Arg Asp Thr Asp Glu Asp Ile
                420                 425                 430

Ala Ala Thr Gly Ala Ser Leu Ser Lys Phe Ser Tyr Thr Thr Val Ser
            435                 440                 445

Ser Leu Gly Pro Ala
        450
```

(2) INFORMATION FOR SEQ ID NO:8:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

```
Leu Thr Ala Pro Gly Pro Gly Ser Gly Ser Arg Pro Thr Gln Ala Lys
1               5                   10                  15

Leu Leu Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
            35                  40                  45

Ala Phe Asp
    50
```

(2) INFORMATION FOR SEQ ID NO:9:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Leu Thr Ala Pro Gly Pro Gly Ser Gly Ser Arg Pro Thr Ala His Val
1               5                   10                  15

Ser Ala Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
            35                  40                  45

Ala Phe Asp
    50
```

(2) INFORMATION FOR SEQ ID NO:10:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Leu Thr Ala Pro Gly Pro Gly Ser Gly Ser Arg Pro Thr Gln Ala Lys
1               5                   10                  15

Ser Ala Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
            35                  40                  45

Ala Phe Asp
    50
```

(2) INFORMATION FOR SEQ ID NO:11:

(i) SEQUENCE CHARACTERISTICS:

(A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Leu Thr Ala Pro Gly Pro Gly Ser Gly Ser Arg Pro Thr Gln Ala Lys
1               5                   10                  15

Ser Leu Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
        35                  40                  45

Ala Phe Asp
    50

(2) INFORMATION FOR SEQ ID NO:12:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

Leu Thr Ala Pro Gly Pro Gly Ser Gly Ser Arg Pro Thr Gln Ala Lys
1               5                   10                  15

Glu Leu Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
        35                  40                  45

Ala Phe Asp
    50

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

Gln Ala Lys Leu Leu
1               5

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

Ala His Tyr Ser Ala
1               5

(2) INFORMATION FOR SEQ ID NO:15:

(i) SEQUENCE CHARACTERISTICS:
       (A) LENGTH: 51 amino acids
       (B) TYPE: amino acid
       (C) STRANDEDNESS: Not Relevant
       (D) TOPOLOGY: linear (ii) MOLECULE TYPE: protein (xi) SEQUENCE DESCRIPTION: SEQ ID NO:15:

Leu Thr Ala Pro Gly Pro Gly Ser Gly Ser Arg Pro Thr Gln Ala Lys
1               5                  10                  15

Leu Leu Ala Lys Lys Arg Val Val Arg Met Leu Leu Val Ile Val Val
                20                  25                  30

Leu Phe Phe Leu Cys Trp Leu Pro Val Tyr Ser Ala Asn Thr Trp Arg
            35                  40                  45

Ala Phe Asp
   50

(2) INFORMATION FOR SEQ ID NO:16:

(i) SEQUENCE CHARACTERISTICS:
       (A) LENGTH: 51 amino acids
       (B) TYPE: amino acid
       (C) STRANDEDNESS: Not Relevant
       (D) TOPOLOGY: linear (ii) MOLECULE TYPE: protein (xi) SEQUENCE DESCRIPTION: SEQ ID NO:16:

Leu Thr Ala Pro Gly Pro Gly Ser Gly Ser Arg Pro Thr Gln Glu Lys
1               5                  10                  15

Glu Leu Glu Lys Lys Arg Glu Glu Arg Met Leu Leu Val Ile Val Val
                20                  25                  30

Leu Phe Phe Leu Cys Trp Leu Pro Val Tyr Ser Ala Asn Thr Trp Arg
            35                  40                  45

Ala Phe Asp
   50

(2) INFORMATION FOR SEQ ID NO:17:

(i) SEQUENCE CHARACTERISTICS:
       (A) LENGTH: 51 amino acids
       (B) TYPE: amino acid
       (C) STRANDEDNESS: Not Relevant
       (D) TOPOLOGY: linear (ii) MOLECULE TYPE: protein (xi) SEQUENCE DESCRIPTION: SEQ ID NO:17:

Leu Thr Ala Pro Gly Pro Gly Ser Gly Ser Arg Pro Thr Gln Glu Lys
1               5                  10                  15

Leu Leu Ala Lys Lys Arg Val Val Arg Met Leu Leu Val Ile Val Val
                20                  25                  30

Leu Phe Phe Leu Cys Trp Leu Pro Val Tyr Ser Ala Asn Thr Trp Arg
            35                  40                  45

Ala Phe Asp
   50

(2) INFORMATION FOR SEQ ID NO:18:

(i) SEQUENCE CHARACTERISTICS:
       (A) LENGTH: 51 amino acids (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

Leu Thr Ala Pro Gly Pro Gly Ser Gly Ser Arg Pro Thr Gln Ala Glu
1               5                   10                  15

Leu Leu Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
        35                  40                  45

Ala Phe Asp
    50

(2) INFORMATION FOR SEQ ID NO:19:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Leu Thr Ala Pro Gly Pro Gly Ser Gly Ser Arg Pro Thr Gln Ala Lys
1               5                   10                  15

Glu Leu Ala Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
        35                  40                  45

Ala Phe Asp
    50

(2) INFORMATION FOR SEQ ID NO:20:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Leu Thr Ala Pro Gly Pro Gly Ser Gly Ser Arg Pro Thr Gln Ala Lys
1               5                   10                  15

Leu Leu Glu Lys Lys Arg Val Val Arg Met Leu Leu Val Ile Val Val
            20                  25                  30

Leu Phe Phe Leu Cys Trp Leu Pro Val Tyr Ser Ala Asn Thr Trp Arg
        35                  40                  45

Ala Phe Asp
    50

(2) INFORMATION FOR SEQ ID NO:21:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear -continued (ii) MOLECULE TYPE: protein (xi) SEQUENCE DESCRIPTION: SEQ ID NO:21:

```
Leu Thr Ala Pro Gly Pro Gly Ser Gly Ser Arg Pro Thr Gln Ala Lys
1               5                   10                  15
Leu Leu Ala Lys Lys Arg Glu Val Arg Met Leu Leu Val Ile Val Val
            20                  25                  30
Leu Phe Phe Leu Cys Trp Leu Pro Val Tyr Ser Ala Asn Thr Trp Arg
        35                  40                  45
Ala Phe Asp
    50
```

(2) INFORMATION FOR SEQ ID NO:22:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

```
Leu Thr Ala Pro Gly Pro Gly Ser Gly Ser Arg Pro Thr Gln Ala Lys
1               5                   10                  15
Leu Leu Ala Lys Lys Arg Val Glu Arg Met Leu Leu Val Ile Val Val
            20                  25                  30
Leu Phe Phe Leu Cys Trp Leu Pro Val Tyr Ser Ala Asn Thr Trp Arg
        35                  40                  45
Ala Phe Asp
    50
```

(2) INFORMATION FOR SEQ ID NO:23:

(i) SEQUENCE CHARACTERISTICS:
        (A) LENGTH: 51 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:23:

```
Leu Thr Ala Pro Gly Pro Gly Ser Gly Ser Arg Pro Thr Gln Ala Lys
1               5                   10                  15
Leu Leu Ala Lys Lys Arg Glu Glu Arg Met Leu Leu Val Ile Val Val
            20                  25                  30
Leu Phe Phe Leu Cys Trp Leu Pro Val Tyr Ser Ala Asn Thr Trp Arg
        35                  40                  45
Ala Phe Asp
    50
```